US009409977B2

(12) United States Patent
Puro

(10) Patent No.: US 9,409,977 B2
(45) Date of Patent: *Aug. 9, 2016

(54) HUMANIZED, ANTI-N2 ANTIBODIES

(71) Applicant: DecImmune Therapeutics, Inc., Cambridge, MA (US)

(72) Inventor: Robyn J. Puro, Brookline, MA (US)

(73) Assignee: DecImmune Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/206,368

(22) Filed: Mar. 12, 2014

(65) Prior Publication Data

US 2014/0271628 A1 Sep. 18, 2014

Related U.S. Application Data

(60) Provisional application No. 61/777,647, filed on Mar. 12, 2013.

(51) Int. Cl.
*C07K 16/18* (2006.01)
*A61K 39/395* (2006.01)
*A61K 39/00* (2006.01)

(52) U.S. Cl.
CPC ............ *C07K 16/18* (2013.01); *A61K 39/39583* (2013.01); *A61K 2039/505* (2013.01); *C07K 2317/24* (2013.01); *C07K 2317/34* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,859,205 A | 1/1999 | Adair et al. | |
| 5,928,893 A | 7/1999 | Kang et al. | |
| 6,753,314 B1 | 6/2004 | Giot et al. | |
| 7,442,783 B2 | 10/2008 | Carroll et al. | |
| 7,863,419 B2 | 1/2011 | Taylor et al. | |
| 8,324,352 B2 | 12/2012 | Carroll | |
| 9,067,983 B2 | 6/2015 | Carroll | |
| 2003/0099656 A1 | 5/2003 | Patti et al. | |
| 2003/0202975 A1 | 10/2003 | Tedder | |
| 2004/0006208 A1 | 1/2004 | Karpusas et al. | |
| 2004/0131607 A1 | 7/2004 | Carroll et al. | |
| 2004/0214272 A1 | 10/2004 | Larosa et al. | |
| 2005/0276811 A1 | 12/2005 | Carroll et al. | |
| 2006/0024296 A1 | 2/2006 | Williams et al. | |
| 2007/0071675 A1 | 3/2007 | Wu et al. | |
| 2007/0135998 A1 | 6/2007 | Van Vlijmen et al. | |
| 2007/0280881 A1 | 12/2007 | Braslawsky et al. | |
| 2008/0260731 A1 | 10/2008 | Bernett et al. | |
| 2008/0262203 A1 | 10/2008 | Clegg et al. | |
| 2009/0176966 A1 | 7/2009 | Carroll et al. | |
| 2009/0299038 A1 | 12/2009 | Nakamura et al. | |
| 2010/0136684 A1 | 6/2010 | Carroll et al. | |
| 2010/0272723 A1 | 10/2010 | Bernett et al. | |
| 2011/0098448 A1 | 4/2011 | Korth et al. | |
| 2012/0082664 A1 | 4/2012 | Bernett et al. | |
| 2012/0093835 A1 | 4/2012 | Carroll | |
| 2014/0056871 A1 | 2/2014 | Carroll | |
| 2014/0271627 A1 | 9/2014 | Puro | |

FOREIGN PATENT DOCUMENTS

| | | |
|---|---|---|
| WO | 9108756 A1 | 6/1991 |
| WO | 9636360 A1 | 11/1996 |
| WO | 0018437 A1 | 4/2000 |
| WO | 0032825 A2 | 6/2000 |
| WO | 0164835 A2 | 9/2001 |
| WO | 0175067 A2 | 10/2001 |
| WO | 0188088 A2 | 11/2001 |
| WO | 0193982 A1 | 12/2001 |
| WO | 03055982 A2 | 7/2003 |
| WO | 2004002210 A2 | 1/2004 |
| WO | 2005085288 A2 | 9/2005 |
| WO | 2011071883 A1 | 6/2011 |

OTHER PUBLICATIONS

Non-Final Office Action from U.S. Appl. No. 14/206,316, dated Mar. 20, 2015.
Restriction Requirement from U.S. Appl. No. 14/206,316, dated Oct. 14, 2014.
Database EMBL [Online], "Mus musculus VH9D5 mRNA for anti-dsRNA (RDV-RNA) antibody, partial cds.", retrieved from EBI accession No. EM STD:AB050071, Database accession No. AB050071, Apr. 2, 2002.
Mus Musculus Myosin Heavy Chain IX (Myh9), mRNA. [online]. [retrieved on Feb. 23, 2015]. GenBank Accession No. NM-022410.
Rudikoff, et al., "Single Amino Acid Substitution Altering Antigen-Binding Specificity," Proc Natl Acad Sci USA 79:1979-1983; Mar. 15, 1982.
Austen, et al., "Self-Reactive Immunoglobulin M from Peritoneal B Cells Mediates Murine Intestinal Ischemia-Reperfusion Injury." Surgical Forum, 1998, vol. 49, pp. 341-342.
Carroll, M.C., "The Role of Complement and Complement Receptors in Induction and Regulation of Immunity." Ann. Rev. Immunol. (1998) 16, 545-568.
Padlan, "Anatomy of the antibody molecule" Molecular Immun. 31 (3) (1994), pp. 169-217.
Hechtman, et al., "Intestinal Ischemia-Reperfusion Injury is Mediated by Natural Antibody derived from Peritoneal Bl-a Cells." FASEB Journal. 1998, vol. 12, p. A34.
Klimka, et al., "Human anti-CD30 recombinant antibodies by guided phage antibody selection using cell panning" British Journal of Cancer (2000) 83: pp. 252-260.
Williams, et al., "Intestinal Reperfusion Injury is Mediated by IgM and Complement," J appl. Physiol, 86:938-942 (1999).
"Aspergillus nidulans FGSC A4 chromosome I ANcontig1.116, whole genome shotgun sequence," GenBank Accession No. AACD0I000116.1, retrieved on Feb. 23, 2015.

(Continued)

*Primary Examiner* — Brian J Gangle
*Assistant Examiner* — Andrea McCollum
(74) *Attorney, Agent, or Firm* — Mahreen Chaudhry Hoda, Esq.; Carolyn S. Elmore, Esq.; Elmore Patent Law Group P.C.

(57) ABSTRACT

The present invention encompasses humanized antibodies that specifically bind N2 peptide, methods for the preparation thereof and methods for the use thereof.

20 Claims, 11 Drawing Sheets

(56) References Cited

OTHER PUBLICATIONS

Weiser, et al., "Reperfusion Injury of Ischemic Skeletal Muscle is Mediated by Natural Antibody and Complement." Journal Experimental Medicine. 1996, vol. 183, pp. 2343-2348.
"Xenopus laevis hypothetical protein LOC398719, mRNA (cDNA clone IMAGE:4889191), partial cds," GenBank accession No. BC057729), retrieved on Feb. 23, 2015.
"Arabidopsis thaliana transcribed RNA for snRNA_08920, complete sequence, ecotype: Col-0," GenBank Accession No. AB957589, retrieved on Feb. 23, 2015.
Zhang, Ming, et al, "Activation of the Lectin Pathway by Natural IgM in a Model of Ischemia/Reperfusion Injury," Journal of Immunology, 177:4272-4734 (2006).
Chan, R.K, et al., "Attenuation of skeletal muscle reperfusion injury with intravenous 12 amino acid peptides that bind to pathogenic IgM," Surgery, pp. 1-8 (2006).
Ahmadi-Yazdi, C., et al., "Attenuation of the Effects of Rat Hemorrhagic Shock with a Reperfusion Injury-Inhibiting Agent Specific to Mice," Shock, 32(3):295-301 (2009).
Haas, M.S., et al., "Blockade of self-reactive IgM significantly reduces injury in a murine model of acute myocardial infarction," Cardiovascular Research, 87:618-627 (2010).
Hofmann, U., et al., "Nothing but natural: targeting natural IgM in ischaemia/reperfusion injury," Cardiovascular Research, 87:589-590 (2010).
Tatlidede, S.H., et al., "Improved Survival of Murine Island Skin Flaps by Prevention of Reperfusion Injury," Plast. Reconstr. Surg., 123(5):1431-1439 (2009).
Suber, F., et al., "Innate response to self-antigen significantly exacerbates burn wound depth," PNAS, 104 (10):3973-3977 (2007).
Huang, J., et al., "Neuronal Protection in Stroke by an sLex-Glycosylated Complement Inhibitory Protein," Science, 285:595-599 (1999).
Zhang, M., et al., "The role of natural IgM in myocardial ischemia-reperfusion injury," J. of Molecular and Cellular Cardiology, 41:62-67 (2006).
Zhang, M, et al., "Identification of the target self-antigens in reperfusion injury," JEM, www.jem.org/cgi/doi/10.1084/jem.20050390, pp. 1-12 (2006).
Yu, et al., "Modulation of Natural IgM Binding and Complement Activation by Natural IgG Antibodies," J. Immunol., 157, pp. 5163-5168, 1996.
"*Homo sapiens* myosin, heavy chain 9, non-muscle, mRNA (cDNA clone IMAGE:5563109), partial cds"; (GenBank accession No. BC049849, retrieved on Feb. 23, 2015).
Beiboer, et al., "Guided selection of a pan carcinoma specific antibody reveals similar binding characteristics yet structural divergence between the original murine antibody and its human equivalent" J. Mol Biol. (2000) 296: pp. 833-849.
Austen, et al., "Murine Hindlimb Reperfusion Injury Can Be Initiated by a Self-Reactive Monoclonal IgM," Surgery, C30 136(2):401-406, (2004).
"*Homo sapiens* mRNA; cDNA DKFZp451 J0218 (from clone DKFZp451 J0218); complete cds" (GenBank accession No. AL832639, retrieved on Feb. 23, 2015).
"Arabidopsis thaliana unknown protein (At3g57990) mRNA, complete cds," GenBank Accession No. AY 122933, retrieved on Feb. 23, 2015.
William, E. Paul, M. D. "Fundamental Immunology" 3rd Edition, 1993, 292-295.
Zhang, et al. "Identification of a Peptide Inhibitor of lschemia/Reperfusion Injury," Molecular Immunology, vol. 41, p. 331 (282), Jun. 2004.
Zhang, et al., Identification of a Specific Self-Reactive IgM Antibody that Initiates Intestinal Ischemia/Reperfusion Injury, PNAS USA 101:3886-91, 2004.
Guo, et al., "Protein Tolerance to Random Amino Acid Change," Proc. Natl. Acad. Sci., 101(25): 9205-10, (2004).
"Nonmuscle Myosin Heavy chain B," (GenBnk accession No. Q27989, retrieved on Feb. 23, 2015).
"Bos taurus nonmuscle myosin heavy chain B mRNA fragment II, partial cds", (GenBank acccession No. UI5693, retrieved on Feb. 23, 2015).
"Oryctolagus curriculus mRNA for myosin heavy chain, partial cds", (rGenBank accession No. D63694, retrieved on Feb. 23, 2015).
Colman, "Effects of Amino Acid Sequence Changes on Antibody-Antigen Interactions," Research in Immunology, 145(1):33-36, 1994.
Paul, "Immunoglobulins: Structure and Function," Fundamental Immunology, Chapter 9, pp. 292-295, 1993.
Copending U.S. Appl. No. 14/967,577, filed Dec. 14, 2015.
Notice of Allowance from U.S. Appl. No. 14/206,316, dated Oct. 2, 2015.
Copending U.S. Appl. No. 14/726,016, filed May 29, 2015.

Sequence comparison of m21G6 and humanized derivatives m21G6 VH
QLQLQQPGAELVKPGASVKLSCKASGYTFTSYYMHWVKQRPGQGLEWIGGINPSNGGTNFNEKFKSKATLTVDKSSSTAYMQLSSLTSEDSAVYYCTRWGYDREWFAYWGQGTLVTVSA

H1-21G6 VH (21/28 CLL)
QVQLVQSGAEVVKPGASVKLSCKASGYTFTSYYMHWVKQAPGQGLEWIGGINPSNGGTNFNEKFKSKATLTVDKSASTAYMELSSLRSEDTAVYYCTRWGYDREWFAYWGQGTLVTVSS

**H2-21G6 VH (Germline HuIgH1-18*01)**
QVQLVQSGAEVKKPGASVKVSCKASGYTFTSYYMYWVRQAPGQGLEWMGIMPSNGGTNFNEKFKSKATMTYDKSTSTAYMELSSLRSDDSAVYYCTRWGYDREWFAYWGQGTLVTVSS

**H3-21G6 VH (Germline HuIgH1-69*06)**
QVQLVQSGAEVKKPGSSVKVSCKASGYTFTSYYMHWVRQAPGQGLEWIGGINPSNGGTNFNEKFKFKATITVDKSTSTAYMELSSLRSEDTAVYYCTRWGYDREWFAYWGQGTLVTVSS m21G6 VL
DVVMTQAAPSVPVTPGESVSISCRSSKSLLHSNGNTYLYWFLQRPGQSPQLLIYRMSNLASGVPDRFSGSGSGTAFTLRISRVEAEDVGVYYCMQHLEYPFTGSGTKLEIKR

L1-21G6 VL (PopVk, CLL)
DIVMTQSPATLSVSPGERATISCRSSKSLLHSNGNTYLYWFQQKPGQPPKVLIYRMSNLASGVPARFSGSGSGTDFTLTISSVEPEDFATYYCMQHLEYPFTFGGGTKLEIKR

**L2-21G6 VL (Germline HuIgKV2-28*01)**
DVVMTQSPLSLPVTPGEPASISCRSSKSLLHSNGNTYLYWFLQKPGQSPQLLIYRMSNLASGVPDRFSGSGSGTDFTLKISRVEAEDVGVYYCMQHLEYPFTFGQGTKLEIKR

**L3-21G6 VL (Germline HuIgKV2-29*02)**
DVVMTQTPLSLSYTPGQPASISCRSSKSLLHSNGNTYLYWFLQRPGQSPQLLIYRMSNLASGVPDRFSGSGSGTDFTLKISRVEAEDVGVYYCMQHLEYPFTFGQGTKLEIKR Bold = amino acid differences between germline sequence and parental m21g6
Italic underline = 
Boxes indicates CDR regions

FIG. 1

Sequence comparison of m21G6 VH region and VH4

FIG. 2 optimized for    Cricetulus griseus

```
                                                              PflMI
                                       AvrII         NcoI
        CACTATAGGGCGAATTGAAGGAAGGCCGTCAAGGCCGCATCCTAGGGCCACCATGGGCTG
    1   ------+---------+---------+---------+---------+---------+
        GTGATATCCCGCTTAACTTCCTTCCGGCAGTTCCGGCGTAGGATCCCGGTGGTACCCGAC
                                                             M  G  W

PvuII
        GTCCTGCATCATCCTGTTTCTGGTCGCCACCGCCACCGGCGTGCACTCCCAGGTCCAGCT
   61   ------+---------+---------+---------+---------+---------+
        CAGGACGTAGTAGGACAAAGACCAGCGGTGGCGGTGGCCGCACGTGAGGGTCCAGGTCGA
         S  C  I  I  L  F  L  V  A  T  A  T  G  V  H  S  Q  V  Q  L

NarI                 NarI
              KasI                 KasI                        StuI
        GGTCCAGTCTGGCGCCGAAGTGAAGAAACCTGGCGCCTCCGTGAAGGTGTCCTGCAAGGC
  121   ------+---------+---------+---------+---------+---------+
        CCAGGTCAGACCGCGGCTTCACTTCTTTGGACCGCGGAGGCACTTCCACAGGACGTTCCG
         V  Q  S  G  A  E  V  K  K  P  G  A  S  V  K  V  S  C  K  A

PflMI
        CTCCGGCTACACCTTCACCAGCTACTACATGTACTGGGTCCGACAGGCCCCAGGCCAGGG
  181   ------+---------+---------+---------+---------+---------+
        GAGGCCGATGTGGAAGTGGTCGATGATGTACATGACCCAGGCTGTCCGGGGTCCGGTCCC
         S  G  Y  T  F  T  S  Y  Y  M  Y  W  V  R  Q  A  P  G  Q  G
```

FIG. 3

```
         ACTGGAATGGATGGGCGGCATCAACCCCTCCAACGGCGGCACCAACTTCAACGAGAAGTT
    241  ------------+------------+------------+------------+------------+
         TGACCTTACCTACCCGCCGTAGTTGGGGAGGTTGCCGCCGTGGTTGAAGTTGCTCTTCAA
          L  E  W  M  G  G  I  N  P  S  N  G  G  T  N  F  N  E  K  F

CAAGTCCAGAGTGACCATGACCACCGACACCTCCACCTCCACCGCCTACATGGAACTGCG
    301  ------------+------------+------------+------------+------------+
         GTTCAGGTCTCACTGGTACTGGTGGCTGTGGAGGTGGAGGTGGCGGATGTACCTTGACGC
          K  S  R  V  T  M  T  T  D  T  S  T  S  T  A  Y  M  E  L  R

GTCCCTGCGGAGCGACGACACCGCCGTGTACTACTGCACCAGATGGGGCTACGACAGAGA
    361  ------------+------------+------------+------------+------------+
         CAGGGACGCCTCGCTGCTGTGGCGGCACATGATGACGTGGTCTACCCCGATGCTGTCTCT
          S  L  R  S  D  D  T  A  V  Y  Y  C  T  R  W  G  Y  D  R  E

ApaI
         GTGGTTCGCCTACTGGGGCCAGGGCACCCTGGTCACAGTGTCCTCGGCTTCCACCAAGGG
    421  ------------+------------+------------+------------+------------+
         CACCAAGCGGATGACCCCGGTCCCGTGGGACCAGTGTCACAGGAGCCGAAGGTGGTTCCC
          W  F  A  Y  W  G  Q  G  T  L  V  T  V  S  S  A  S  T  K  G

CCCCTCCGTGTTCCCTCTGGCCCCCTCCAGCAAGTCCACCTCTGGCGGCACCGCTGCCCT
    481  ------------+------------+------------+------------+------------+
         GGGGAGGCACAAGGGAGACCGGGGGAGGTCGTTCAGGTGGAGACCGCCGTGGCGACGGGA
          P  S  V  F  P  L  A  P  S  S  K  S  T  S  G  G  T  A  A  L

NarI
                                                                    KasI
         GGGCTGCCTGGTCAAAGACTACTTCCCCGAGCCCGTGACCGTGTCCTGGAACTCTGGCGC
    541  ------------+------------+------------+------------+------------+
         CCCGACGGACCAGTTTCTGATGAAGGGGCTCGGGCACTGGCACAGGACCTTGAGACCGCG
          G  C  L  V  K  D  Y  F  P  E  P  V  T  V  S  W  N  S  G  A
```

```
          GGTGTCTGTGCTGACCGTGCTGCACCAGGACTGGCTGAACGGCAAGGAGTACAAGTGCAA
1021      ------------+------------+------------+------------+------------+
          CCACAGACACGACTGGCACGACGTGGTCCTGACCGACTTGCCGTTTCTCATGTTCACGTT
           V  S  V  L  T  V  L  H  Q  D  W  L  N  G  K  E  Y  K  C  K

BsaI
          GGTCTCCAACAAGGCCCTGCCTGCCCCCATCGAAAAGACCATCTCCAAGGCCAAGGGCCA
1081      ------------+------------+------------+------------+------------+
          CCAGAGGTTGTTCCGGGACGGACGGGGGTAGCTTTTCTGGTAGAGGTTCCGGTTCCCGGT
           V  S  N  K  A  L  P  A  P  I  E  K  T  I  S  K  A  K  G  Q

GCCCCGGGAGCCCCAGGTGTACACACTGCCCCCTAGCCGGGAAGAGATGACCAAGAACCA
1141      ------------+------------+------------+------------+------------+
          CGGGGCCCTCGGGGTCCACATGTGTGACGGGGGATCGGCCCTTCTCTACTGGTTCTTGGT
           P  R  E  P  Q  V  Y  T  L  P  P  S  R  E  E  M  T  K  N  Q

GGTGTCCCTGACCTGTCTGGTCAAAGGCTTCTACCCCTCCGACATTGCCGTGGAATGGGA
1201      ------------+------------+------------+------------+------------+
          CCACAGGGACTGGACAGACCAGTTTCCGAAGATGGGGAGGCTGTAACGGCACCTTACCCT
           V  S  L  T  C  L  V  K  G  F  Y  P  S  D  I  A  V  E  W  E

GTCCAACGGCCAGCCGGAGAACAACTACAAGACCACCCCCCCTGTGCTGGACTCCGACGG
1261      ------------+------------+------------+------------+------------+
          CAGGTTGCCGGTCGGCCTCTTGTTGATGTTCTGGTGGGGGGACACGACCTGAGGCTGCC
           S  N  G  Q  P  E  N  N  Y  K  T  T  P  P  V  L  D  S  D  G

CTCATTCTTCCTGTACTCCAAGCTGACCGTGGACAAGTCCCGGTGGCAGCAGGGCAACGT
1321      ------------+------------+------------+------------+------------+
          GAGTAAGAAGGACATGAGGTTCGACTGGCACCTGTTCAGGGCCACCGTCGTCCCGTTGCA
           S  F  F  L  Y  S  K  L  T  V  D  K  S  R  W  Q  Q  G  N  V

GTTCTCCTGCTCCGTGATGCACGAGGCCCTGCACAACCACTACACCCAGAAGTCCCTGTC
1381      ------------+------------+------------+------------+------------+
          CAAGAGGACGAGGCACTACGTGCTCCGGGACGTGTTGGTGATGTGGGTCTTCAGGGACAG
           F  S  C  S  V  M  H  E  A  L  H  N  H  Y  T  Q  K  S  L  S
```

FIG. 3 (cont.)

```
                    BstZ17I
                    AccI
       CCTGAGCCCCCGGCAAGTGATGAGTATACCTGGGCCTCATGGGCCTTCCTTTCACTGCCCG
1441   ------------+------------+------------+------------+------------+------------+
       GGACTCGGGGCCGTTCACTACTCATATGGACCCGGAGTACCCGGAAGGAAAGTGACGGGC
        L  S  P  G  K  *

CTTTCCAG
1501   --------
       GAAAGGTC
```

FIG. 3 (cont.)

optimized for          Cricetulus griseus

```
                                                                    PflMI
                                       SacI     EcoRV     NcoI
          CGAATTCGCGGAAGGCCGTCAAGGCCACGTGTCTTGTCCAGAGCTCGATATCGCCACCAT
     1    ------------+---------+---------+---------+---------+---------+
          GCTTAAGCGCCTTCCGGCAGTTCCGGTGCACAGAACAGGTCTCGAGCTATAGCGGTGGTA
                                                                        M

GGGCTGGTCCTGCATCATCCTGTTTCTGGTCGCCACCGCCACCGGCGTGCACGGCGACAT
    61    ------------+---------+---------+---------+---------+---------+
          CCCGACCAGGACGTAGTAGGACAAAGACCAGCGGTGGCGGTGGCCGCACGTGCCGCTGTA
           G  W  S  C  I  I  L  F  L  V  A  T  A  T  G  V  H  G  D  I

CGTGATGACCCAGTCCCCCCTGTCCCTGCCCGTGACACCTGGCGAGCCTGCCTCCATCTC
   121    ------------+---------+---------+---------+---------+---------+
          GCACTACTGGGTCAGGGGGGACAGGGACGGGCACTGTGGACCGCTCGGACGGAGGTAGAG
           V  M  T  Q  S  P  L  S  L  P  V  T  P  G  E  P  A  S  I  S

PscI
          CTGCCGGTCCTCCAAGTCCCTGCTGCACTCCAACGGCAATACCTACCTGTACTGGTTCCT
   181    ------------+---------+---------+---------+---------+---------+
          GACGGCCAGGAGGTTCAGGGACGACGTGAGGTTGCCGTTATGGATGGACATGACCAAGGA
           C  R  S  S  K  S  L  L  H  S  N  G  N  T  Y  L  Y  W  F  L

PvuII
          GCAGAAGCCCGGCCAGTCCCCTCAGCTGCTGATCTACCGGATGTCCAACCTGGCCTCCGG
   241    ------------+---------+---------+---------+---------+---------+
          CGTCTTCGGGCCGGTCAGGGGAGTCGACGACTAGATGGCCTACAGGTTGGACCGGAGGCC
           Q  K  P  G  Q  S  P  Q  L  L  I  Y  R  M  S  N  L  A  S  G
```

```
        CACCCTGACCCTGTCCAAGGCCGACTACGAGAAGCACAAGGTGTACGCCTGCGAAGTGAC
661     ------------+---------+---------+---------+---------+---------+
        GTGGGACTGGGACAGGTTCCGGCTGATGCTCTTCGTGTTCCACATGCGGACGCTTCACTG
         T  L  T  L  S  K  A  D  Y  E  K  H  K  V  Y  A  C  E  V  T
```

```
                                                                PacI
        CCACCAGGGCCTGTCCAGCCCCGTGACCAAGTCCTTCAACCGGGGCGAGTGCTGATGATT
721     ------------+---------+---------+---------+---------+---------+
        GGTGGTCCCGGACAGGTCGGGGCACTGGTTCAGGAAGTTGGCCCCGCTCACGACTACTAA
         H  Q  G  L  S  S  P  V  T  K  S  F  N  R  G  E  C  *  *
```

```
            KpnI
        AATTAAGGTACCTGGAGCACAAGACTGGCCTCATGGGCCTTCCGGCTCACTGC
781     ------------+---------+---------+---------+---------+--
        TTAATTCCATGGACCTCGTGTTCTGACCGGAGTACCCGGAAGGCGAGTGACG
```

FIG. 4 (cont.)

HUMANIZED, ANTI-N2 ANTIBODIES

RELATED APPLICATION

This application claims the benefit of U.S. Provisional Application No. 61/777,647, filed Mar. 12, 2013. The entire teachings of the above application are incorporated herein by reference.

GOVERNMENT SUPPORT

The invention was supported, in whole or in part, by Grant No. 5R44HL084821-03 from the National Institutes of Health. The Government has certain rights in the invention.

BACKGROUND OF THE INVENTION

It has been demonstrated that ischemia-reperfusion injury can be initiated by clonally-specific pathogenic IgM that activates the classical pathway of complement (Zhang et al. (2004) *Proc. Natl. Acad. Sci.* 101(11):3886-3891). Pathogenic IgM (also referred to as "natural IgM") recognizes and binds to a self-antigen which is an antigen expressed or exposed on damaged tissue, for example, on damaged ischemic tissue. Binding of pathogenic IgM to the self-antigen initiates inflammation by activating complement in the classical pathway. U.S. Pat. No. 7,442,783 describes the major epitope for binding of natural IgMs as a conserved region within type II non-muscle myosin heavy chain (NMHC) proteins. This epitope is referred to as the N2 12-mer peptide.

Inhibitors of the interaction between the N2 epitope and pathogenic IgM have been described as useful for the treatment of inflammatory diseases and conditions, including ischemia/reperfusion injury. For example, U.S. Pat. No. 8,324,352 describes the murine monoclonal antibody referred to as 21G6. Murine 21G6 (m21G6) was shown to bind to the N2 peptide and provide protection against ischemia/reperfusion injury in animal models. It would be advantageous to develop additional therapeutic agents that bind the N2 peptide and that can be used for treating inflammatory conditions such as ischemia/reperfusion injury.

SUMMARY OF THE INVENTION

The present invention encompasses humanized derivatives of the murine 21G6 antibody that specifically bind N2 peptide. As shown in the Examples below, humanized antibodies have been developed that bind the N2 peptide.

In one embodiment, the invention is directed to an antibody or antigen binding fragment thereof comprising framework regions from a human immunoglobulin and comprising the variable heavy chain (VH) complementarity determining regions (CDRs) of the murine 21G6 antibody and the variable light chain (VL) CDRs of the murine 21G6 antibody.

In some embodiments, the invention is directed to a humanized, anti-N2 antibody or antigen-binding fragment thereof comprising a heavy chain variable (VH) region and a light chain variable (VL) region, wherein:
  i. the VH region comprises three complementarity determining regions (CDRs) VH CDR1, VH CDR2 and VH CDR3 wherein the VH CDR1 comprises SEQ ID NO: 3, VH CDR2 comprises SEQ ID NO: 4 and VH CDR3 comprises SEQ ID NO: 5;
  ii. the VH region comprises four framework regions (FWR) VH FWR1, VH FWR2, VH FWR3 and VH FWR4 wherein:
    a. the VH FWR1 comprises SEQ ID NO: 15, SEQ ID NO: 19 or SEQ ID NO: 23;
    b. The VH FWR2 comprises SEQ ID NO: 16, SEQ ID NO: 20 or SEQ ID NO: 24;
    c. VH FWR3 comprises SEQ ID NO: 17, SEQ ID NO: 21, SEQ ID NO: 25, SEQ ID NO: 43, SEQ ID NO: 44 or SEQ ID NO: 45; and
    d. VH FWR4 comprises SEQ ID NO: 18, SEQ ID NO: 22, or SEQ ID NO: 26;
  iii. the VL region comprises three complementarity determining regions (CDRs) VL CDR1, VL CDR2 and VL CDR3, wherein the VL CDR1 comprises SEQ ID NO: 6, VL CDR2 comprises SEQ ID NO: 7 and VL CDR3 comprises SEQ ID NO: 8;
  iv. the VL region comprises four framework regions (FWR) VL FWR1, VL FWR2, VL FWR3 and VL FWR4 wherein:
    a. the VL FWR1 comprises SEQ ID NO: 27, SEQ ID NO: 31, or SEQ ID NO: 35;
    b. VL FWR2 comprises SEQ ID NO: 28, SEQ ID NO: 32, or SEQ ID NO: 36;
    c. VL FWR3 comprises SEQ ID NO: 29, SEQ ID NO: 33, or SEQ ID NO: 37; and
    d. VL FWR4 comprises SEQ ID NO: 30, SEQ ID NO: 34, or SEQ ID NO: 38.

In certain additional embodiments, the antibody or antigen-binding fragment has a VH region that comprises a sequence selected from the group consisting of SEQ ID NO: 9, SEQ ID NO: 10 and SEQ ID NO: 11. In yet additional embodiments, the antibody or antigen-binding fragment has a VH region that comprises a sequence selected from the group consisting of SEQ ID NO: 9, SEQ ID NO: 10, SEQ ID NO: 11 and SEQ ID NO: 49.

In additional aspects, the antibody or antigen-binding fragment has a VL region that comprises a sequence selected from the group consisting of SEQ ID NO: 12, SEQ ID NO: 13 and SEQ ID NO: 14.

In yet additional aspects, the antibody or antigen-binding fragment has a VH region that consists of SEQ ID NO: 9 and has a VL region that consists of SEQ ID NO: 12. In other embodiments, the antibody or antigen-binding fragment has a VH region that consists of SEQ ID NO: 9 and has a VL region that consists of SEQ ID NO: 13. In another aspect, the antibody or antigen-binding fragment has a VH region that consists of SEQ ID NO: 9 and the VL region consists of SEQ ID NO: 14. In a further embodiment, the antibody or antigen-binding fragment has a VH region that consists of SEQ ID NO: 10 and has a VL region consists of SEQ ID NO: 12. In certain additional aspects, the antibody or antigen-binding fragment has a VH region that consists of SEQ ID NO: 10 and has a VL region that consists of SEQ ID NO: 13. In an additional embodiment, the antibody or antigen-binding fragment has a VH region that consists of SEQ ID NO: 10 and has a VL region that consists of SEQ ID NO: 14. In another aspect of the invention, the antibody or antigen-binding fragment of has a VH region that consists of SEQ ID NO: 11 and a VL region that consists of SEQ ID NO: 12.

In another embodiment, the antibody or antigen-binding fragment has a VH region that consists of SEQ ID NO: 11 and a VL region that consists of SEQ ID NO: 13. In another embodiment, the antibody or antigen-binding fragment has a VH region that consists of SEQ ID NO: 11 and a VL region that consists of SEQ ID NO: 14. In yet additional embodiments, the antibody or antigen-binding fragment of has a VH region that consists of SEQ ID NO: 49 and a VL region that consists of SEQ ID NO: 12. In another embodiment, the antibody or antigen-binding fragment has a VH region that consists of SEQ ID NO: 49 and a VL region that consists of SEQ ID NO: 13. In another embodiment, the antibody or antigen-binding fragment has a VH region that consists of SEQ ID NO: 49 and a VL region that consists of SEQ ID NO: 14.

In some embodiments, the antibody or antigen-binding fragment has a VH region that consists of SEQ ID NO: 43 and a VL region that consists of a sequence selected from the group consisting of SEQ ID NO: 12, SEQ ID NO: 13 and SEQ ID NO: 14. In additional embodiments, the antibody or antigen-binding fragment has a VH region that consists of SEQ ID NO: 44 and a VL region that consists of a sequence selected from the group consisting of SEQ ID NO: 12, SEQ ID NO: 13 and SEQ ID NO: 14. In yet other embodiments, the antibody or antigen-binding fragment has a VH region that consists of SEQ ID NO: 45 and a VL region that consists of a sequence selected from the group consisting of SEQ ID NO: 12, SEQ ID NO: 13 and SEQ ID NO: 14. In another aspect, the invention is an antibody or antigen-binding fragment has a VH region that consists of SEQ ID NO: 42 and VL region consists of a sequence selected from the group consisting of SEQ ID NO: 12, SEQ ID NO: 13 and SEQ ID NO: 14.

In yet additional embodiments, the invention is directed to a humanized, anti-N2 antibody or antigen-binding fragment thereof comprising a heavy chain variable (VH) region comprising a sequence selected from the group consisting of SEQ ID NO: 9, SEQ ID NO: 10 and SEQ ID NO: 11. In an additional embodiment, the invention is directed to a humanized, anti-N2 antibody or antigen-binding fragment thereof comprising a heavy chain variable (VH) region comprising a sequence selected from the group consisting of SEQ ID NO: 9, SEQ ID NO: 10, SEQ ID NO: 11 and SEQ ID NO: 49.

In a further embodiment, the invention is a humanized, anti-N2 antibody or antigen-binding fragment thereof, comprising a light chain variable (VL) region comprising a sequence selected from the group consisting of SEQ ID NO: 12, SEQ ID NO: 13 and SEQ ID NO: 14.

In certain embodiments, the invention is directed to a humanized, anti-N2 antibody or antigen-binding fragment thereof comprising a heavy chain variable (VH) region and a light chain variable (VL) region, wherein:

i. the VH region comprises three complementarity determining regions (CDRs) VH CDR1, VH CDR2 and VH CDR3 wherein the VH CDR1 comprises SEQ ID NO: 3, VH CDR2 comprises SEQ ID NO: 4 and VH CDR3 comprises SEQ ID NO: 5;

ii. the VH region comprises four framework regions (FWR) VH FWR1, VH FWR2, VH FWR3 and VH FWR4 wherein:

a. the VH FWR1 comprises SEQ ID NO: 15, SEQ ID NO: 19 or SEQ ID NO: 23;

b. The VH FWR2 comprises SEQ ID NO: 16, SEQ ID NO: 20, SEQ ID NO:24 or SEQ ID NO: 50;

c. VH FWR3 comprises SEQ ID NO: 17, SEQ ID NO: 21, SEQ ID NO: 25, SEQ ID NO: 43, SEQ ID NO: 44, SEQ ID NO: 45, SEQ ID NO: 51 or SEQ ID NO: 52; and d. VH FWR4 comprises SEQ ID NO: 18, SEQ ID NO: 22, or SEQ ID NO: 26;

iii. the VL region comprises three complementarity determining regions (CDRs) VL CDR1, VL CDR2 and VL CDR3 wherein the VL CDR1 comprises SEQ ID NO: 6, VH CDR2 comprises SEQ ID NO: 7 and VH CDR3 comprises SEQ ID NO: 8;

iv. the VL region comprises four framework regions (FWR) VL FWR1, VL FWR2, VL FWR3 and VL FWR4 wherein:

a. the VL FWR1 comprises SEQ ID NO: 27, SEQ ID NO: 31, or SEQ ID NO: 35;

b. VL FWR2 comprises SEQ ID NO: 28, SEQ ID NO: 32, or SEQ ID NO: 36;

c. VL FWR3 comprises SEQ ID NO: 29, SEQ ID NO: 33, or SEQ ID NO: 37; and d. VL FWR4 comprises SEQ ID NO: 30, SEQ ID NO: 34, or SEQ ID NO: 38.

In certain additional embodiments, the antibody or antigen-binding fragment has a VH region that comprises a sequence selected from the group consisting of SEQ ID NO: 9, SEQ ID NO: 10, SEQ ID NO: 11 and SEQ ID NO: 49. In additional aspects, the antibody or antigen-binding fragment has a VL region that comprises a sequence selected from the group consisting of SEQ ID NO: 12, SEQ ID NO: 13 and SEQ ID NO: 14.

In yet additional embodiments, the antibody or antigen binding fragment has a VH that consists of the amino acid sequence of SEQ ID NO: 49 and the VL region consists of the amino acid sequence of SEQ ID NO: 12. In yet other embodiments, the antibody or antigen-binding fragment has a VH region that consists of the amino acid sequence of SEQ ID NO: 49 and the VL region consists of the amino acid sequence of SEQ ID NO: 13. In yet further embodiments, the antibody or antigen-binding fragment has a VH region consists of the amino acid sequence of SEQ ID NO: 49 and the VL region consists of the amino acid sequence of SEQ ID NO: 14. In yet an additional aspect, the antibody or antigen-binding fragment has a VH region that consists of the amino acid sequence of SEQ ID NO: 54 and VL region consists of a sequence selected from the group consisting of SEQ ID NO: 12, SEQ ID NO: 13 and SEQ ID NO: 14.

In further embodiments, the invention is directed to a nucleotide encoding the humanized, anti-N2 antibody or antigen-binding fragment thereof.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 shows a sequence comparison of the murine 21G6 heavy chain variable (VH) region (SEQ ID NO: 1) and the humanized heavy chain variable regions (VH) H1, H2 and H3 (SEQ ID NOS: 9-11, respectively) and also shows a sequence comparison of the murine 21G6 light chain variable (VL) region (SEQ ID NO: 2) and the humanized light chain variable regions light chain (VL) regions L1, L2 and L3 (SEQ ID NOS: 12-14, respectively). The CDR regions are indicated by the boxes.

FIG. 2 shows a sequence comparison of murine 21G6 heavy chain (VH) region (SEQ ID NO: 1) and the humanized heavy chain variable region H4 (SEQ ID NO: 49).

FIG. 3 shows a nucleotide sequence (SEQ ID NO: 60) encoding the humanized heavy chain variable region H4 that was optimized for the production of the humanized antibody in Chinese hamster ovary (CHO) cells. FIG. 3 also shows the amino acid sequence of the heavy chain variable region H4 SEQ ID NO: 54). Each + indicates where a change was made as compared to (SEQ ID NO: 66).

FIG. 4 shows a nucleotide sequence (SEQ ID NO: 69) encoding the humanized light chain variable region L2 that was optimized for the production of the humanized antibody in Chinese hamster ovary (CHO) cells. FIG. 4 also shows the amino acid of the light chain variable region L2 SEQ ID NO: 55). Each + indicates where a change was made as compared to (SEQ ID NO: 67).

DETAILED DESCRIPTION OF THE INVENTION

Figure 5:
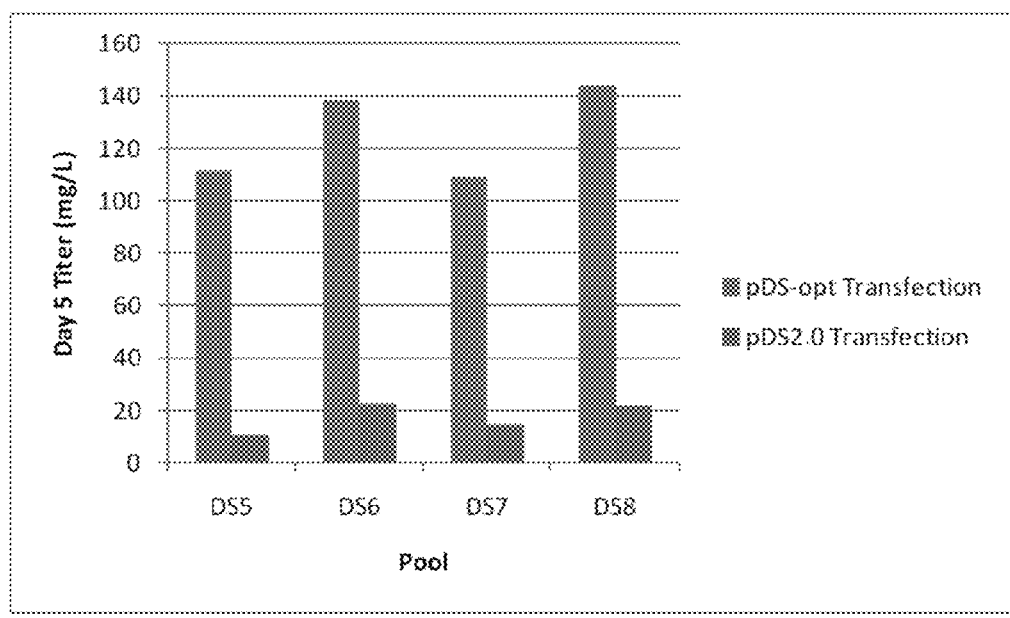
FIG. 5 is a bar graph showing the levels of recombinant antibody expression on day 5 post-transfection with either the native sequences (pDS2.0; bars on the right) or optimized sequences (pDS-opt; bars on the left). Incorporation of the recombinant antibody into the CHO cells was accomplished by selection in the presence of 10 ug/ml puromycin and 100 nM methotrexate for transfectants DS5 and DS7 or 20 ug/ml puromycin/200 nM methotrexate for transfectants DS6 and DS8.

A description of preferred embodiments of the invention follows.

The words "a" or "an" are meant to encompass one or more, unless otherwise specified.

An "antibody" is a binding molecule including immunoglobulin molecules, antibody fragments, and immunologically active portions of immunoglobulin molecules, for example, molecules that contain an antigen-binding site. Native antibodies and immunoglobulins are usually heterotetrameric glycoproteins of about 150,000 daltons, composed of two identical light chains and two identical heavy chains. Each heavy chain has at one end a variable domain followed by a number of constant domains. Each light chain has a variable domain at one end and a constant domain at its other end. An antibody binds specifically to an antigen (or other molecule) if the antibody binds preferentially to the antigen, and, for example, has less than about 30%, preferably less than about 20%, less than about 10%, or less than about 1% cross-reactivity with another molecule. The terms "antibody" and "immunoglobulin" are used interchangeably. "Bind" or "binding" are used herein to refer to detectable relationships or associations (e.g. biochemical interactions) between molecules.

An "isolated" molecule, for example, an isolated antibody or isolated peptide, refers to a condition of being separate or purified from other molecules present in the natural environment or as they occur in nature.

The N2 epitope is an epitope of the self-antigen, the 12 amino acid sequence expressed in non-muscle myosin heavy chain (NMHC) type II. The 12-amino acid sequence is LMKNMDPLNDNV (SEQ ID NO: 47). The N2 epitope is described in detail in U.S. Pat. No. 7,442,783, the contents of which are expressly incorporated by reference herein. "Natural IgM" or "pathogenic IgM" refers to an IgM antibody that is naturally produced in a mammal (for example, a human) that binds to the N2 epitope and initiates inflammation by activating complement in the classical pathway.

In some embodiments, antibody or antigen-binding fragment thereof binds to SEQ ID NO: 47. In additional embodiments, the antibody or antigen-binding fragment thereof binds to an epitope wherein the amino acid sequence of the epitope has at least about 80%, 85%, 90%, 95%, or 98% sequence identity to the amino acid sequence of SEQ ID NO: 47. In certain embodiments, the epitope comprises the amino acid sequence LMKNMDPLNDNI (SEQ ID NO: 48).

The hypervariable region of an antibody or fragment thereof refers to the amino acid residues that contribute to antigen-binding. The hypervariable region comprises amino acid residues from the complementarity determining regions (CDRs). The CDRs are specific regions within variable regions of the heavy and the light chain. Generally, the variable region consists of four framework regions (FWR1, FWR2, FWR3, FWR4) and three CDRs arranged as follows: NH$_2$-FWR1-CDR1-FWR2-CDR2-FWR3-CDR3-FWR4-constant region-C(O)OH. The term "framework regions" refers to those variable domain amino acid residues other than the CDR residues and include, for example, FWR1, FWR2, FWR3, and FWR4.

As described above, the present invention is directed to humanized derivatives of the murine 21G6 antibody described in U.S. Pat. No. 8,324,352, the contents of which are expressly incorporated herein. In certain embodiments, the humanized antibodies and fragments thereof bind the N2 peptide. The amino acid sequences of the heavy chain variable region (VH) and the light chain variable region (VL) of the murine 21G6 antibody are shown in FIG. 1 and are below as SEQ ID NOs: 1 and 2:

```
Murine 21G6 (m21G6) VH
                                           (SEQ ID NO: 1)
QVQLQQPGAELVKPGASVKLSCKASGYTFTSYYMYWVKQRPGQGLEWIG

GINPSNGGTNFNEKFKSKATLTVDKSSSTAYMQLSSLTSEDSAVYYCTRW

GYDREWFAYWGQGTLVTVSA.

Murine 21G6 VL
                                           (SEQ ID NO: 2)
DIVMTQAAPSVPVTPGESVSISCRSSKSLLHSNGNTYLYWFLQRPGQSP

QVLIYRMSNLASGVPDRFSGSGSGTAFTLRISRVEAEDVGVYYCMQHLEY

PFTFGSGTKLEIKR.
```

The underlined amino acids represent the complementarity determining regions.

FIG. 1 shows the amino acid sequences of three VH regions encompassed by the invention: H1-21G6, H2-21G6 and H3-21G6. The amino acid sequences of the H1-21G6, H2-21G6 and H3-21G6 VH regions are SEQ ID NOs: 9, 10 and 11, respectively:

```
H1-21G6 VH
                                           (SEQ ID NO: 9)
QVQLVQSGAEVVKPGASVKLSCKASGYTFTSYYMYWVKQAPGQGLEW

IGGINPSNGGTNFNEKFKSKATLTVDKSASTAYMELSSLRSEDTAVY

YCTRWGYDREWFAYWGQGTLVTVSS.

H2-21G6 VH
                                           (SEQ ID NO: 10)
QVQLVQSGAEVKKPGASVKVSCKASGYTFTSYYMYWVRQAPGQGLEW

IGGINPSNGGTNFNEKFKSKATMTVDKSTSTAYMELRSLRSDDSAVY

YCTRWGYDREWFAYWGQGTLVTVSS.

H3-21G6 VH
                                           (SEQ ID NO: 11)
QVQLVQSGAEVKKPGSSVKVSCKASGYTFTSYYMYWVRQAPGQGLEW

IGGINPSNGGTNFNEKFKSKATITVDKSTSTAYMELSSLRSEDTAVY

YCTRWGYDREWFAYWGQGTLVTVSS.
```

The underlined amino acids represent the complementarity determining regions.

An additional VH region is also encompassed by the invention: H4-21G6. The amino acid sequence of H4-21G6 is shown below:

H4-21G6 Vh
(SEQ ID NO: 49)
QVQLVQSGAEVKKPGASVKVSCKASGYTFT<u>SYYMY</u>WVRQAPGQGLEW

MG<u>GINPSNGGTNFNEKFKS</u>RVTMTTDTSTSTAYMELRSLRSDDTAVYYCT

R<u>WGYDREWFAY</u>WGQGTLVTVSS

The Figure also shows the amino acid sequences of three VL regions encompassed by the invention: L1-21G6, L2-21G6 and L3-21G6. The amino acid sequences of L1-21G6, L2-21G6 and L3-21G6 VH regions are SEQ ID NOs: 12, 13 and 14, respectively.

L1-21G6 VL
(SEQ ID NO: 12)
DIVMTQSPATLSVSPGERATISC<u>RSSKSLLHSNGNTYLY</u>WFQQKP

GQPPKVLIY<u>RMSNLAS</u>GVPARFSGSGSGTDFTLTISSVEPEDFATYY

C<u>MQHLEYPFT</u>FGGGTKLEIKR.

L2-21G6 VL
(SEQ ID NO: 13)
DIVMTQSPLSLPVTPGEPASISC<u>RSSKSLLHSNGNTYLY</u>WFLQKPGQSP

QLLIY<u>RMSNLAS</u>GVPDRFSGSGSGTDFTLKISRVEAEDVGVYYC

<u>MQHLEYPFT</u>FGQGTKLEIKR.

L3-21G6 VL
(SEQ ID NO: 14)
DIVMTQTPLSLSYTPGQPASISC<u>RSSKSLLHSNGNTYLY</u>WFLQKPGQS

PQLLIY<u>RMSNLAS</u>GVPDRFSGSGSGTDFTLKISRVEAEDVGVYYC

<u>MQHLEYPFT</u>FGQGTKLEIKR.

The underlined amino acids represent the complementarity determining regions.

The names "H1-21G6," "H2-21G6," "H3-21G6" and "H4-21G6" are used interchangeably herein with "H1," "H2," "H3," and "H4," respectively. The names "L1-21G6," "L2-21G6" and "L3-21G6" are used interchangeably with "L1," "L2" and "L3," respectively.

CDR1, CDR2 and CDR3 of the VH regions of the antibodies or fragments of the present invention are SYYMY (SEQ ID NO: 3), GINPSNGGTNFNEKFKS (SEQ ID NO: 4), GYDREWFAY (SEQ ID NO: 5), respectively. CDR1, CDR2 and CDR3 of the VL regions of the antibodies or fragments of the present invention are RSSKSLLHSNGNTYLY (SEQ ID NO: 6), RMSNLAS (SEQ ID NO: 7), and MQHLEYPFT (SEQ ID NO: 8), respectively. The VL region of the antibody or antigen-binding fragments of the present invention includes at least two of the CDRs of m21G6 VL. The VH region of the antibody or antigen-binding fragment of the invention includes at least two CDRs of the m21G6 VH. In some embodiments, the humanized antibodies include all three CDRs of m21G6 VH and/or all three CDRs of the m21G6 VL. The framework regions FWR1, FWR2, FWR3 and FWR4 of the VH region of each of H1-21G6, H2-21G6 and H3-21G6 are shown below:

H1 VH FWR1
(SEQ ID NO: 15)
QVQLVQSGAEVVKPGASVKLSCKASGYTFT.

H1 VH FWR2
(SEQ ID NO: 16)
WVKQAPGQGLEWIG.

H1 VH FWR3
(SEQ ID NO: 17)
KATLTVDKSASTAYMELSSLRSEDTAVYYCTR.

H1 VH FWR4
(SEQ ID NO: 18)
WGQGTLVTVSS.

H2 VH FWR1
(SEQ ID NO: 19)
QVQLVQSGAEVKKPGASVKVSCKASGYTFT.

H2 VH FWR2
(SEQ ID NO: 20)
WVRQAPGQGLEWIG.

H2 VH FWR3
(SEQ ID NO: 21)
KATMTVDKSTSTAYMELRSLRSDDSAVYYCTR.

H2 VH FWR4
(SEQ ID NO: 22)
WGQGTLVTVSS.

H3 VH FWR1
(SEQ ID NO: 23)
QVQLVQSGAEVKKPGSSVKVSCKASGYTFT.

H3 VH FWR2
(SEQ ID NO: 24)
WVRQAPGQGLEWIG.

H3 VH FWR3
(SEQ ID NO: 25)
KATITVDKSTSTAYMELSSLRSEDTAVYYCTR.

H3 VH FWR4
(SEQ ID NO: 26)
WGQGTLVTVSS.

H4 VH FWR1
(SEQ ID NO: 19)
QVQLVQSGAEVKKPGASVKVSCKASGYTFT.

H4 VH FWR2
(SEQ ID NO: 50)
WVRQAPGQGLEWMG.

H4 VH FWR3
(SEQ ID NO: 51)
RVTMTTDTSTSTAYMELRSLRSDDTAVYYCTR.

H4 VH FWR4
(SEQ ID NO: 22)
WGQGTLVTVSS.

The framework regions FWR1, FWR2, FWR3 and FWR4 of each of the VL region of each of L1-21G6, L2-21G6 and L3-21G6 are shown below:

L1 VL FWR1
(SEQ ID NO: 27)
DIVMTQSPATLSVSPGERATISC.

L1 VL FWR2
(SEQ ID NO: 28)
WFQQKPGQPPKVLIY.

L1 VL FWR3
(SEQ ID NO: 29)
GVPARFSGSGSGTDFTLTISSVEPEDFATYYC.

L1 VL FWR4
(SEQ ID NO: 30)
FGGGTKLEIKR.

L2 VL FWR1
(SEQ ID NO: 31)
DIVMTQSPLSLPVTPGEPASISC.

-continued

L2 VL FWR2
(SEQ ID NO: 32)
WFLQKPGQSPQLLIY.

L2 VL FWR3
(SEQ ID NO: 33)
GVPDRFSGSGSGTDFTLKISRVEAEDVGVYYC.

L2 VL FWR4
(SEQ ID NO: 34)
FGQGTKLEIKR.

L3 VL FWR1
(SEQ ID NO: 35)
DIVMTQTPLSLSYTPGQPASISC.

L3 VL FWR2
(SEQ ID NO: 36)
WFLQKPGQSPQLLIY.

L3 VL FWR3
(SEQ ID NO: 37)
GVPDRFSGSGSGTDFTLKISRVEAEDVGVYYC.

L3 VL FWR4
(SEQ ID NO: 38)
FGQGTKLEIKR.

As described above, the present invention encompasses an antibody or antigen-binding fragment thereof comprising VH CDR1, CDR2 and CDR3 having the amino acid sequences SEQ ID NO: 3, SEQ ID NO: 4 and SEQ ID NO: 5, respectively, and VL CDR1, CDR2 and CDR3 having the amino acid sequences SEQ ID NO: 6, SEQ ID NO: 7 and SEQ ID NO: 8, respectively, and further comprising a VH region that comprises four framework regions (FWR) VH FWR1, VH FWR2, VH FWR3 and VH FWR4 wherein:
  a. the VH FWR1 comprises SEQ ID NO: 15, SEQ ID NO: 19 or SEQ ID NO: 23;
  b. The VH FWR2 comprises SEQ ID NO: 16, SEQ ID NO: 20 or SEQ ID NO:24;
  c. VH FWR3 comprises SEQ ID NO: 17, SEQ ID NO: 21, SEQ ID NO: 25, SEQ ID NO: 43, SEQ ID NO: 44 or SEQ ID NO: 45; and
  d. VH FWR4 comprises SEQ ID NO: 18, SEQ ID NO: 22, or SEQ ID NO: 26;
and a VL region that comprises four framework regions (FWR) VL FWR1, VL FWR2, VL FWR3 and VL FWR4 wherein:
  a. the VL FWR1 comprises SEQ ID NO: 27, SEQ ID NO: 31, or SEQ ID NO: 35;
  b. VL FWR2 comprises SEQ ID NO: 28, SEQ ID NO: 32, or SEQ ID NO: 36;
  c. VL FWR3 comprises SEQ ID NO: 29, SEQ ID NO: 33, or SEQ ID NO: 37; and
  d. VL FWR4 comprises SEQ ID NO: 30, SEQ ID NO: 34, or SEQ ID NO: 38.

The present invention additionally encompasses an antibody or antigen-binding fragment thereof comprising VH CDR1, CDR2 and CDR3 having the amino acid sequences SEQ ID NO: 3, SEQ ID NO: 4 and SEQ ID NO: 5, respectively, and VL CDR1, CDR2 and CDR3 having the amino acid sequences SEQ ID NO: 6, SEQ ID NO: 7 and SEQ ID NO: 8, respectively, and further comprising a VH region that comprises four framework regions (FWR) VH FWR1, VH FWR2, VH FWR3 and VH FWR4 wherein:
  a. the VH FWR1 comprises SEQ ID NO: 15, SEQ ID NO: 19, SEQ ID NO: 23;
  b. The VH FWR2 comprises SEQ ID NO: 16, SEQ ID NO: 20 or SEQ ID NO:24 or SEQ ID NO: 50;
  c. VH FWR3 comprises SEQ ID NO: 17, SEQ ID NO: 21, SEQ ID NO: 25, SEQ ID NO: 43, SEQ ID NO: 44, SEQ ID NO: 45, SEQ ID NO: 51 or SEQ ID NO: 52; and
  d. VH FWR4 comprises SEQ ID NO: 18, SEQ ID NO: 22, or SEQ ID NO: 26;
and a VL region that comprises four framework regions (FWR) VL FWR1, VL FWR2, VL FWR3 and VL FWR4 wherein:
  a. the VL FWR1 comprises SEQ ID NO: 27, SEQ ID NO: 31, or SEQ ID NO: 35;
  b. VL FWR2 comprises SEQ ID NO: 28, SEQ ID NO: 32, or SEQ ID NO: 36;
  c. VL FWR3 comprises SEQ ID NO: 29, SEQ ID NO: 33, or SEQ ID NO: 37; and
  d. VL FWR4 comprises SEQ ID NO: 30, SEQ ID NO: 34, or SEQ ID NO: 38.

The terms "comprises" and "comprising" permits (but does not require) the inclusion of additional elements. For example, in the context of an amino acid sequence, the terms "comprises" and "comprising" permits the inclusion of additional amino acids at either the N-terminus and/or the carboxy terminal end. In some embodiments, the framework region of the VH and VL regions comprise a specific indicated amino acid sequence and one to three additional amino acids at the N-terminus and/or at the carboxy terminal end.

In certain additional aspects, the antibody or antigen binding fragment of the invention comprises a heavy chain variable (VH) region and a light chain variable (VL) region, wherein:
  i. the VH comprises three complementarity determining regions (CDRs) VH CDR1, VH CDR2 and VH CDR3 wherein the VH CDR1 consists of SEQ ID NO:3, VH CDR2 consists of SEQ ID NO: 4 and VH CDR3 consists of SEQ ID NO: 5;
  ii. the VH region comprises four framework regions (FWR) VH FWR1, VH FWR2, VH FWR3 and VH FWR4 wherein:
    a. the VH FWR1 consists of SEQ ID NO: 15, SEQ ID NO: 19 or SEQ ID NO: 23;
    b. The VH FWR2 consists of SEQ ID NO: 16, SEQ ID NO: 20 or SEQ ID NO:24;
    c. VH FWR3 comprises SEQ ID NO: 17, SEQ ID NO: 21, SEQ ID NO: 25, SEQ ID NO: 43, SEQ ID NO: 44 or SEQ ID NO: 45; and
    d. VH FWR4 consists of SEQ ID NO: 18, SEQ ID NO: 22, or SEQ ID NO: 26;
  iii. the VL region comprises three complementarity determining regions (CDRs) VL CDR1, VL CDR2 and VL CDR3 wherein the VL CDR1 consists of SEQ ID NO: 6, VH CDR2 comprises SEQ ID NO: 7 and VH CDR3 consists of SEQ ID NO: 8;
  iv. the VL region comprises four framework regions (FWR) VL FWR1, VL FWR2, VL FWR3 and VL FWR4 wherein:
    a. the VL FWR1 consists of SEQ ID NO: 27, SEQ ID NO: 31, or SEQ ID NO: 35;
    b. VL FWR2 consists of SEQ ID NO: 28, SEQ ID NO: 32, or SEQ ID NO: 36;
    c. VL FWR3 consists of SEQ ID NO: 29, SEQ ID NO: 33, or SEQ ID NO: 37;
    d. VL FWR4 consists of SEQ ID NO: 30, SEQ ID NO: 34, or SEQ ID NO: 38.

In yet additional embodiments, the present invention additionally encompasses an antibody or antigen-binding fragment thereof comprising VH CDR1, CDR2 and CDR3 having the amino acid sequences SEQ ID NO: 3, SEQ ID NO: 4 and SEQ ID NO: 5, respectively, and VL CDR1, CDR2 and CDR3 having the amino acid sequences SEQ ID NO: 6, SEQ ID NO: 7 and SEQ ID NO: 8, respectively, and further comprising a VH region that comprises four framework regions (FWR) VH FWR1, VH FWR2, VH FWR3 and VH FWR4 wherein:
  a. the VH FWR1 consists of SEQ ID NO: 15, SEQ ID NO: 19, SEQ ID NO: 23;
  b. The VH FWR2 consists of SEQ ID NO: 16, SEQ ID NO: 20 or SEQ ID NO:24 or SEQ ID NO: 50;
  c. VH FWR3 consists of SEQ ID NO: 17, SEQ ID NO: 21, SEQ ID NO: 25, SEQ ID NO: 43, SEQ ID NO: 44, SEQ ID NO: 45, SEQ ID NO: 51 or SEQ ID NO: 52; and
  d. VH FWR4 consists of SEQ ID NO: 18, SEQ ID NO: 22, or SEQ ID NO: 26;
and a VL region that comprises four framework regions (FWR) VL FWR1, VL FWR2, VL FWR3 and VL FWR4 wherein:
  e. the VL FWR1 consists of SEQ ID NO: 27, SEQ ID NO: 31, or SEQ ID NO: 35;
  f. VL FWR2 consists of SEQ ID NO: 28, SEQ ID NO: 32, or SEQ ID NO: 36;
  g. VL FWR3 consists of SEQ ID NO: 29, SEQ ID NO: 33, or SEQ ID NO: 37; and
  h. VL FWR4 consists of SEQ ID NO: 30, SEQ ID NO: 34, or SEQ ID NO: 38.

As described above, FIG. 1 shows the amino acid sequences of three exemplary humanized VH regions that comprise the VH CDRs of m21G6 (H1-21G6, H2-21G6 and H3-21G6; SEQ ID NOs: 9, 10 and 11, respectively). An additional exemplary humanized VH region that comprises the VH CDRs of m21G6 is H4-21G6 (SEQ ID NO: 49 or SEQ ID NO: 54). FIG. 1 also shows the amino acid sequences of three exemplary humanized VL regions (L1-21G6, L2-21G6 and L3-21G6; SEQ ID NOs: 12, 13 and 14, respectively). In some embodiments, the antibody or antigen-binding fragments of the invention comprise a VH region that comprises a sequence selected from the group consisting of SEQ ID NO: 9, SEQ ID NO: 10 and SEQ ID NO: 11. In yet an additional embodiment, the antibody or antigen-binding fragment comprises a VH region that comprises a sequence selected from the group consisting of SEQ ID NO: 9, SEQ ID NO: 10, SEQ ID NO: 11, SEQ ID NO: 49 and SEQ ID NO: 54, and comprises a VL region that comprises a sequence selected from the group consisting of SEQ ID NO: 12, SEQ ID NO: 13 and SEQ ID NO: 14. In additional embodiments, the antibody or antigen-binding fragments of the invention comprise a VH region that comprises a sequence selected from the group consisting of SEQ ID NO: 9, SEQ ID NO: 10, SEQ ID NO: 11, SEQ ID NO: 49 and SEQ ID NO: 54. In additional aspects, the antibody or antigen-binding fragment has a VL region that comprises a sequence selected from the group consisting of SEQ ID NO: 12, SEQ ID NO: 13 and SEQ ID NO: 14. In yet another embodiment, the antibody or antigen-binding fragment comprises a VH region that comprises a sequence selected from the group consisting of SEQ ID NO: 9, SEQ ID NO: 10 and SEQ ID NO: 11 and comprises a VL region that comprises a sequence selected from the group consisting of SEQ ID NO: 12, SEQ ID NO: 13 and SEQ ID NO: 14.

In some embodiments, the antibody or antigen-binding fragment has a VH region that comprises or consists of SEQ ID NO: 9 and has a VL region that comprises or consists of SEQ ID NO: 12. In other embodiments, the antibody or antigen-binding fragment has a VH region that comprises or consists of SEQ ID NO: 9 and has a VL region that comprises or consists of SEQ ID NO: 13. In another aspect, the antibody or antigen-binding fragment has a VH region that comprises or consists of SEQ ID NO: 9 and the VL region comprises or consists of SEQ ID NO: 14. In a further embodiment, the antibody or antigen-binding fragment has a VH region that comprises or consists of SEQ ID NO: 10 and has a VL region that comprises or consists of SEQ ID NO: 12. In certain additional aspects, the antibody or antigen-binding fragment has a VH region that comprises or consists of SEQ ID NO: 10 and has a VL region that comprises or consists of SEQ ID NO: 13. In an additional embodiment, the antibody or antigen-binding fragment has a VH region that comprises or consists of SEQ ID NO: 10 and has a VL region that comprises or consists of SEQ ID NO: 14. In another aspect of the invention, the antibody or antigen-binding fragment of claim 1 has a VH region that comprises or consists of SEQ ID NO: 11 and a VL region that comprises or consists of SEQ ID NO: 12. In another embodiment, the antibody or antigen-binding fragment has a VH region that comprises or consists of SEQ ID NO: 11 and a VL region that comprises or consists of SEQ ID NO: 13. In another embodiment, the antibody or antigen-binding fragment has a VH region that comprises or consists of SEQ ID NO: 11 and a VL region that comprises or consists of SEQ ID NO: 14.

In yet additional embodiments, the antibody or antigen-binding fragment has a VH region that comprises or consists of SEQ ID NO: 49 and has a VL region that comprises or consists of SEQ ID NO: 12. In another aspect, the antibody or antigen-binding fragment has a VH region that comprises or consists of SEQ ID NO: 49 and the VL region comprises or consists of SEQ ID NO: 13. In a further embodiment, the antibody or antigen-binding fragment has a VH region that comprises or consists of SEQ ID NO: 49 and has a VL region that comprises or consists of SEQ ID NO: 14.

In certain additional embodiments, the antibody or antigen-binding fragment comprises a VH region that comprises a sequence selected from SEQ ID NO: 49 and SEQ ID NO: 54. In yet additional embodiments, the antibody or antigen-binding fragment comprises a VL region that comprises SEQ ID NO: 13 or SEQ ID NO: 55. In a further embodiment, the antibody or antigen-binding fragment comprises a VH region that comprises SEQ ID NO: 49 or SEQ ID NO: 54 and a VL region that comprises SEQ ID NO: 13 or SEQ ID NO: 55. In an additional aspect, the antibody or antigen-binding fragment comprising a VH region that comprises SEQ ID NO: 49 and a VL region that comprises SEQ ID NO: 13.

In certain aspects of the invention, the isotype of the constant region of the antibodies or antigen-binding fragments of the invention is IgG1, IgG2, IgG3, or IgG4. In some embodiments, the isotype of the IgG constant region is IgG1. In other embodiments, the isotype of the IgG constant region is IgG4. In some embodiments, the antibody or antigen-binding fragment thereof have a human IgG1 constant domain or a human IgG4 constant domain. In additional aspects, the antibody or antigen-binding fragment has a human Ig kappa constant domain. The term "isotype" refers to the classification of an antibody's heavy or light chain constant region. The constant domains of antibodies are not involved in binding to antigen, but have various effector functions. Depending on the amino acid sequence of the heavy chain constant region, a human or humanized antibody can be deemed to belong to one of five major classes of immunoglobulins: IgA, IgD, IgE, IgG, and IgM. Many of these classes of immunoglobulins, for example the IgG class, can be divided into subclasses (isotypes), for example, IgG1, IgG2, IgG3, and IgG4. Human light chain constant regions are classified into two major classes, kappa and lambda.

When the positions of amino acid residues are referred to by number herein, it is to be understood that Kabat numbering system is used, unless otherwise indicated. Kabat numbering is described in Kabat et al. (1991) Sequences of Proteins of Immunological Interest, Publication No. 91-3242, National Institutes of Health, National Technical Information Service (hereinafter "Kabat"). Immunoglobulin sequences can be numbered according to Kabat by performing an alignment with the Kabat reference sequence. As such, the Kabat numbering system provides a uniform system for numbering immunoglobulin chains.

The present invention is directed to humanized antibodies wherein the CDRs are from the murine 21G6 antibody and wherein the framework regions are from a human immunoglobulin. It will be understood, that humanized antibodies can comprise amino acid residues that are not found in the recipient antibody or in the donor antibody. For example, such changes in the amino acid sequence can be made to improve binding to the antigen (for example, the N2 peptide) and/or to reduce immunogenicity. Therefore, the present invention encompasses the antibodies or antigen-binding fragments described herein wherein specific amino acids have been substituted, deleted or added. Amino acid substitutions, deletions or additions can be made to the antibodies or antigen-binding fragments thereof to improve or refine the properties of the antibody or fragment, for example amino acid change can be made to inhibit or block inflammation. For example, asparagine at position 297 (Asn 297) of the IgG constant region can be replaced with an alternative amino acid to reduce glycosylation and decrease activation of complement and binding to the Fc receptor. See, for example, Leatherbarrow et al. (1985) Effector functions of a monoclonal aglycosylated mouse IgG2a: binding and activation of complement component C1 and interaction with human monocyte Fc receptor. *Mol Immunol* 22(4):407-415; Tao et al. (1989) Studies of aglycosylated chimeric mouse-human IgG. Role of carbohydrate in the structure and effector functions mediated by the human IgG constant region. *J Immunol* 143(8):2595-2601; Kabat (1987) Sequences of Proteins of Immunological Interest (In: US Department of Human Services), and Sazinsky et al. (2008), Aglycosylated immunoglobulin $G_1$ variants productively engage activating Fc receptors, *PNAS* 105(51): 20167-20172, the contents of each of which are expressly incorporated by reference herein. Glycosylation can be reduced, for example, by replacing the asparagine at position 297 (Asn 297) with an alternative amino acid, for example, alanine, glutamine, histidine or glycine. In some embodiments, Asn 297 can be replaced with glutamine. In certain aspects, the antibody or antigen-binding fragment has a human IgG1 constant domain that is aglycosylated.

In some embodiments, the penultimate amino acid in the third framework of the VH (VH FWR3) of each of H1-21G6, H2-21G6 and H3-21G6 (SEQ ID NOs: 17, 21 and 25, respectively) can be changed from threonine to alanine. The amino acid sequences SEQ ID NOs: 39, 40 and 41 are sequences for the VH FWR3 of each of H1, H2 and H3 wherein the penultimate amino acid (threonine) has been replaced with alanine:

```
H1 VH FWR3 with amino acid mutation to alanine
                                   (SEQ ID NO: 39)
KATLTVDKSASTAYMELSSLRSEDTAVYYCAR.

H2 VH FWR3 with amino acid mutation to alanine
                                   (SEQ ID NO: 40)
KATMTVDKSTSTAYMELRSLRSDDSAVYYCAR.

H3 VH FWR3 with amino acid mutation to alanine
                                   (SEQ ID NO: 41)
KATITVDKSTSTAYMELSSLRSEDTAVYYCAR.
```

The italicized alanine above represents the change from threonine to alanine. The amino acid sequences SEQ ID NOs: 43, 44, and 45 are sequences for the H1, H2 and H3 VH regions wherein the penultimate amino acid (threonine) of the FWR3 is replaced with alanine:

```
H1 VH with amino acid mutation to alanine in FWR3
                                   (SEQ ID NO: 43)
QVQLVQSGAEVVKPGASVKLSCKASGYTFTSYYMYWVKQAPGQGLEW

IGGINPSNGGTNFNEKFKSKATLTVDKSASTAYMELSSLRSEDTAVYY

CARWGYDREWFAYWGQGTLVTVSS.

H2 VH with amino acid mutation to alanine in FWR3
                                   (SEQ ID NO: 44)
QVQLVQSGAEVKKPGASVKVSCKASGYTFTSYYMYWVRQAPGQGLEW

IGGINPSNGGTNFNEKFKSKATMTVDKSTSTAYMELRSLRSDDSAVYY

CARWGYDREWFAYWGQGTLVTVSS.

H3 with amino acid mutation to alanine in FWR3
                                   (SEQ ID NO: 45)
QVQLVQSGAEVKKPGSSVKVSCKASGYTFTSYYMYWVRQAPGQGLEWI

GGINPSNGGTNFNEKFKSKATITVDKSTSTAYMELSSLRSEDTAVYYCA

RWGYDREWFAYWGQGTLVTVSS.
```

The italicized alanine above represents the change from threonine to alanine.

In an additional embodiment, the penultimate amino acid in the third framework regions of the VH (VH FWR3) of H4-21G6 (SEQ ID NO: 51) can be changed from threonine to alanine. The amino acid sequence SEQ ID NO: 52 is the sequence for the VH FWR3 of H4 wherein the penultimate amino acid (threonine has been replaced with alanine:

```
    H4 VH FWR3
                                   (SEQ ID NO: 52)
         RVTMTTDTSTSTAYMELRSLRSDDTAVYYCAR.
```

The italicized alanine above represents the change from threonine to alanine. The amino acid sequence SEQ ID NO: 52 is the sequence for the H4 VH regions wherein the penultimate amino acid (threonine) of the FWR3 is replaced with alanine:

```
H4 VH with amino acid mutation to alanine in FWR3
                                   (SEQ ID NO: 53)
QVQLVQSGAEVKKPGASVKVSCKASGYTFTSYYMYWVRQAPGQGLEWM

GGINPSNGGTNFNEKFKSRVTMTTDTSTSTAYMELRSLRSDDTAVYYC

ARWGYDREWFAYWGQGTLVTVSS.
```

The italicized alanine above represents the change from threonine to alanine.

Amino acid modifications that may increase stability and/or increase affinity are also contemplated herein. Additional specific amino acid variants contemplated by the invention are variants of H2-21G6 VH and a variant of the murine 21G6 VL kappa chain:

Amino Acid Variant of H2 VH
(SEQ ID NO: 42)
QVQLVQSGAELVKKPGASLKVSCKASGYTFTSYYMYWVRQAPGQGLEWI

GGINPSNGGTNFNEKFKGRVTITRDKSTSTAYMELRSLRSEDSAVYYCA

RWGYDREWFAYWGQGTLVTVSS.

Amino Acid Variant of kappa chain (m21G6 VL)
(SEQ ID NO: 46)
EIVLTQSPGTLSLSP GERATLSCRAS KSLLHSNGNTYLYWYQQKPGQA

PRLLIYRMSNRATGIPA RFSGSGSGTDFTLTISSLEPEDFAVYYC MQH

LEYPFTFGQGTKLEIKR.

Additional amino acid modifications include amino acid variants of the H2 VH amino acid sequence (SEQ ID NO: 42), wherein the amino acid at position 65 is replaced with glycine, the amino acid at position 66 is replaced with arginine, the amino acid at position 67 is replaced with valine or phenylalanine, the amino acid at position 69 is replaced with isoleucine, the amino acid at position 71 is replaced with arginine and/or the amino acid at position 85 can be replaced with glutamic acid.

The invention also encompasses an antibody or antigen-binding fragment thereof wherein an alanine at position 78 (Ala 78) of the VH is replaced with phenylalanine.

In certain embodiments, the antibody or antigen-binding fragment has a human IgG4 constant domain wherein serine at position 228 (Ser 228) is replaced with proline.

Additional modifications can also be made within the Fc region, typically to alter one or more functional properties of the antibody, such as serum half-life, complement fixation, Fc receptor binding, protein stability and/or antigen-dependent cellular cytotoxicity, or lack thereof. In addition, an antibody of the invention can be chemically modified (e.g., one or more chemical moieties can be attached to the antibody). In addition, the class of an antibody can be "switched" by known techniques. Such techniques include, e.g., the use of direct recombinant techniques (see e.g., U.S. Pat. No. 4,816,397) and cell-cell fusion techniques (see e.g., U.S. Pat. No. 5,916, 771). For example, an antibody that was originally produced as an IgM molecule may be class switched to an IgG antibody. Class switching techniques also may be used to convert one IgG subclass to another, e.g., from IgG1 to IgG2. Thus, the effector function of the antibodies of the invention may be changed by isotype switching to, e.g., an IgG1, IgG2, IgG3, IgG4, IgD, IgA, IgE, or IgM antibody for various therapeutic uses. Exemplary cDNA sequences for constant regions are available from GenBank, for example, each of which incorporated by reference in its entirety, are as follows: Human IgG1 constant heavy chain region: GenBank Accession No.: J00228; Human IgG2 constant heavy chain region: GenBank Accession No.: J00230; Human IgG3 constant heavy chain region: GenBank Accession No.: X04646; Human IgG4 constant heavy chain region: GenBank Accession No.: K01316; and Human kappa light chain constant region: GenBank Accession No.: J00241. The hinge region of $CH_1$ can also be modified such that the number of cysteine residues in the hinge region is increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody. The Fc hinge region of an antibody can also be mutated to decrease the biological half-life of the antibody. In another embodiment, the antibody is modified to increase its biological half-life. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. In yet other embodiments, the Fc region is altered by replacing at least one amino acid residue with a different amino acid residue to alter the effecter function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both to Winter et al. In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In another example, one or more amino acid residues within amino acid positions 231 and 239 are altered to thereby alter the ability of the antibody to fix complement. This approach is described further in PCT Publication WO 94/29351 by Bodmer et al. In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al. (2001) J. Biol. Chem. 276:6591-6604).

In addition, the half-life of an antibody molecule can be increased by increasing the affinity of the antibody for the Fc receptor (FcR). The binding of the antibody to the FcR can be improved using art-known techniques, such as by introducing specific mutations in the Fc region (Dall'Acqua, W. F. et al. (2006) J. Biol. Chem. 281: 23514-23524; Petkova, S. B. (2006) et al., Internat. Immunol. 18:1759-1769; U.S. Pat. Nos. 7,785,791, 7,790,858 and 7,371,826; the contents of each of the aforementioned references are incorporated by reference herein). It has been demonstrated that the increased affinity of the antibody for the FcR results in a longer half-life (Petkova et al., 2006). In the case of amino acid mutagenesis in the Fc domain, it is known that certain amino acid mutations can increase binding to the FcR and extend the half-life. Examples of such amino acid mutations that have been described to increase binding to the Fc receptor include N434A and T307/E380/N434 (Petkova et al., 2006) and as well other mutations M252Y/S254T/T256E, T250Q, M428L, and T250Q/M428L, (Dall'Acqua et al., 2006; Hinton et al., J. Immunol., 176: 346-356).

An antibody or antigen-binding fragment described herein can be chemically modified based on linkage to a polymer. The polymer is typically water soluble so that the antibody to which it is attached does not precipitate in an aqueous environment, such as a physiological environment. The polymer can have a single reactive group, such as an active ester for acylation or an aldehyde for alkylation, so that the degree of polymerization may be controlled. An exemplary reactive aldehyde is polyethylene glycol propionaldehyde, which is water stable, or mono $C_1$-$C_{10}$ alkoxy or aryloxy derivatives thereof (see U.S. Pat. No. 5,252,714). The polymer can be branched or unbranched. For therapeutic use of the end-product preparation, the polymer is pharmaceutically acceptable. The water soluble polymer, or mixture thereof if desired, can be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

An antibody fragment or antigen-binding fragment is a derivative of an antibody that is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv, diabody, minibody, Fc, Fd fragments, and single chain antibodies.

Antibody fragments can be produced by methods known in the art. For example, the antibody fragment can be enzymatically or chemically produced by fragmentation of an intact antibody, or the fragment can be produced recombinantly. The antibody fragment can optionally be a single chain antibody fragment. Alternatively, the fragment can comprise multiple chains which are linked together, for instance, by disulfide linkages. In addition, digestion of an antibody with pepsin yields F(ab')$_2$ fragments and multiple small fragments. Mercaptoethanol reduction of an antibody yields individual heavy and light chains. Digestion of an antibody with papain yields individual Fab fragments and the Fc fragment. The fragment can also optionally be a multimolecular complex. A functional antibody fragment can for example comprise at least about 50 amino acids. In some embodiments, the functional antibody fragment can comprise at least about 200 amino acids.

Humanized antibodies and antigen-binding fragment thereof described herein can be produced using techniques known in the art, including, but not limited to, CDR-grafting (see, for example, European Patent No. EP 239,400; WO 91/09967; and U.S. Pat. Nos. 5,225,539, 5,530,101, and 5,585,089, the contents of each of which incorporated by reference), veneering or resurfacing (see, for example, European Patent Nos. EP 592,106 and EP 519,596; Padlan, 1991, Molecular Immunology 28(4/5):489-498; Studnicka et al., 1994, Protein Engineering, 7(6):805-814; and Roguska et al., 1994, Proc. Natl. Acad. Sci., 91:969-973, each of which is incorporated herein by its entirety by reference), chain shuffling (see, e.g., U.S. Pat. No. 5,565,332, which is incorporated herein in its entirety by reference), and techniques disclosed in, for example, U.S. Pat. Nos. 6,407,213, 5,766,886, PCT Publication No. WO 9317105, Tan et al., J. Immunol., 169: 1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al, Protein Eng., 9(10):895-904 (1996), Couto et al., Cancer Res., 55 (23 Supp): 5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated by reference herein.

The humanized antibody can be produced by, for example, by constructing cDNAs encoding the humanized variable regions, inserting each of them into an expression vector for animal cells comprising genes encoding the heavy chain and light chain of a human antibody to thereby construct a vector for expression of humanized antibody, and introducing it into an animal cell to express and produce the humanized antibody. The invention encompasses a nucleotide sequence that encodes an antibody or antigen-binding fragment described herein. In additional embodiments, the invention is directed to a nucleotide sequence that encodes an antibody or fragment thereof comprising a heavy chain or VH described herein. In certain embodiments, the nucleotide sequence comprises a sequence that encodes the VH region of H1-21G6, H2-21G6, H3-21G6, or H4-21G6. Exemplary nucleotide sequences include SEQ ID NOs: 56, 57, 58, and 59 respectively (shown below). In some embodiments, the nucleotide sequence that encodes an antibody described herein comprises a sequence selected from the group consisting of SEQ ID NOs: 56, 57, 58, and 59. In some embodiments, the nucleotide sequence is SEQ ID NO: 59. In certain additional embodiments, the invention encompasses a nucleotide sequence that encodes an antibody of fragment thereof that comprises a nucleotide that encodes a light chain or VL described herein. Exemplary nucleotide sequences encoding the VL regions L1-21G6, L2-21G6 and L3-21G6 are SEQ ID NOs: 61, 62 and 63, respectively (shown below). In some embodiments, the nucleotide sequence that encodes an antibody described herein comprises a sequence selected from the group consisting of SEQ ID NOs: 61, 62 and 63. In yet additional embodiments, the nucleotide sequence that encodes an antibody of antigen-binding fragment thereof comprises a sequence selected from the group consisting of SEQ ID NOs: 56, 57, 58, and 59 and a sequence selected from the group consisting of SEQ ID NOs: 61, 62 and 63. In yet additional embodiments, the nucleotide sequence comprises SEQ ID NO: 59 and SEQ ID NO: 62.

Figure 3:
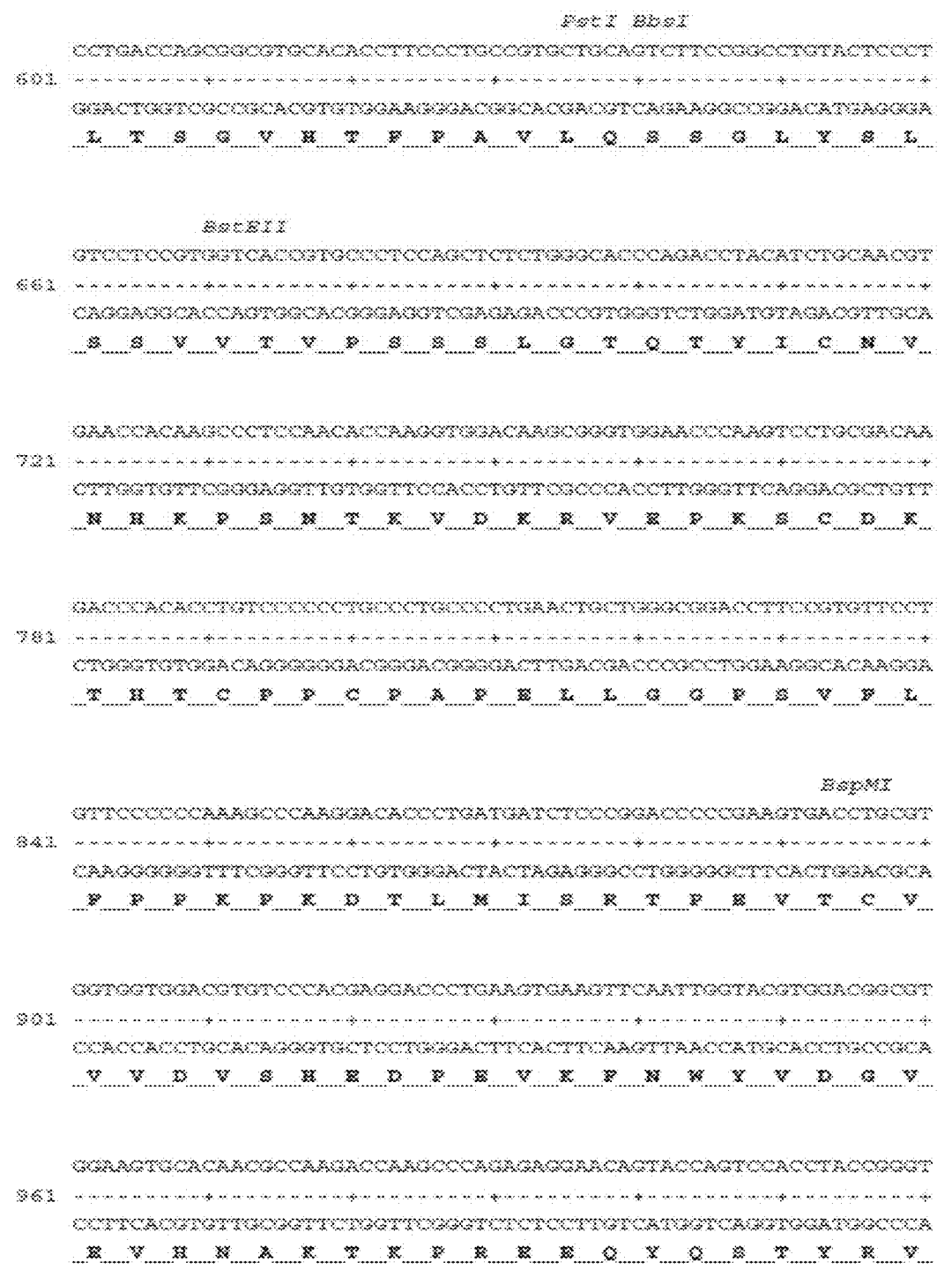
Figure 4:
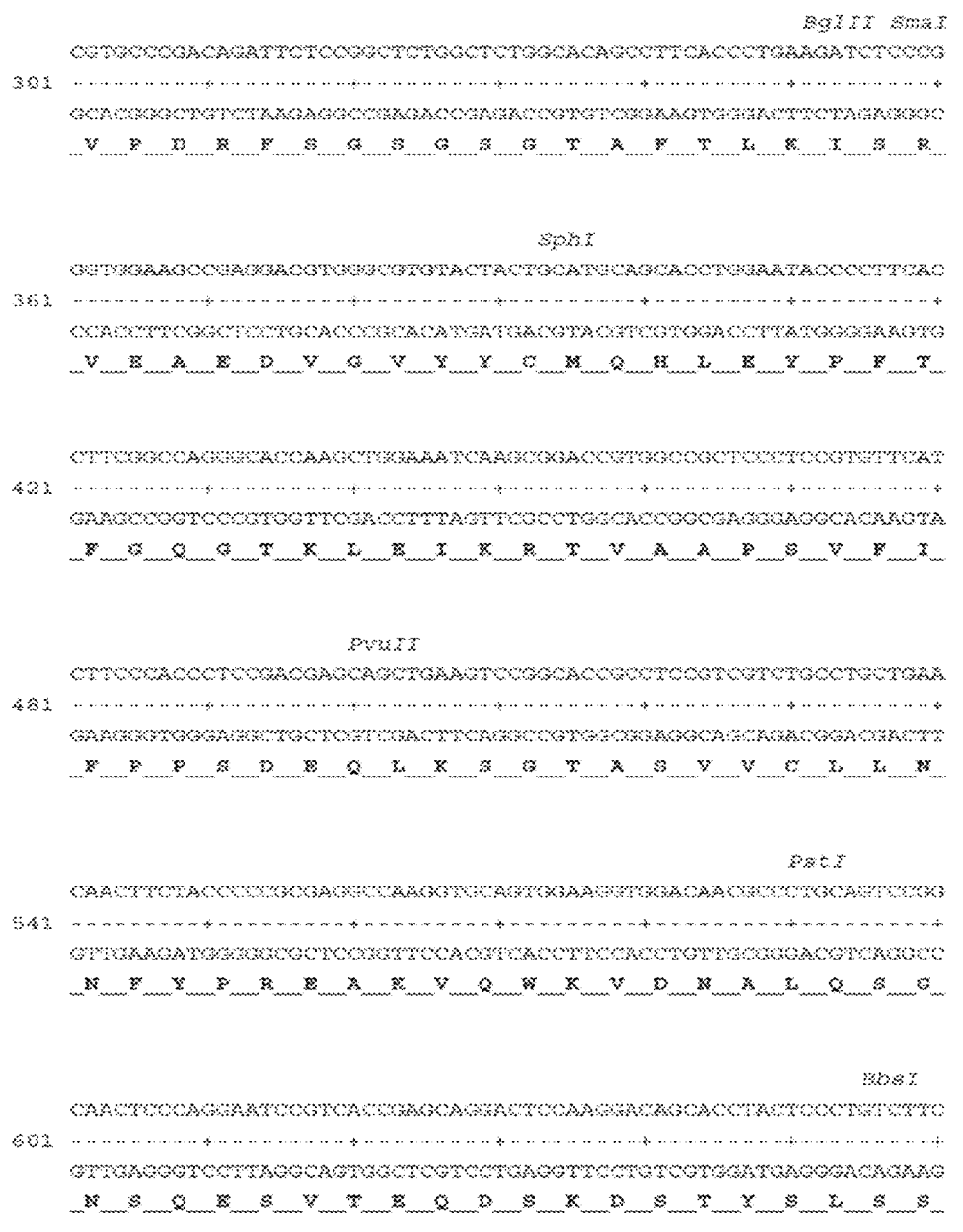

Also encompassed herein are nucleotide sequences that encode antibody, VH and/or VL regions described herein and that are optimized for increased production in specific expression systems. An exemplary method for optimizing expression of mRNA and/or protein is the GENEOPTIMIZER® Process from LifeTechnologies (see, for example, www.lifetechnologies.com/us/en/home/life-science/cloning/gene-synthesis/geneart-gene-synthesis/geneoptimizer.html). As shown in FIGS. 3 to 5, SEQ ID NOs: 64, 65, 68 and 69 represent optimized nucleotide sequences for production of the H4-21G6 Vh and L2 -21G6 V1 regions in CHO cells. In some embodiments, the invention encompasses a nucleotide sequence of SEQ ID NO: 64. In additional embodiments, the invention encompasses a nucleotide sequence of SEQ ID NO: 65. In yet further embodiments, the nucleotide comprises SEQ ID NO: 64 and SEQ ID NO: 65.

Also encompassed is an expression vector comprising a nucleotide sequence that encodes an antibody or antigen-binding fragment, a VH region and/or a VL region of the invention and an isolated cell comprising said vector. The antibody or antigen-binding fragment, can be produced, for example, by culturing a cell comprising said expression vector, recovering the antibody or fragment thereof from the cultured cells or culture medium. In some embodiments, the antibody or antigen-binding fragment is produced by culturing CHO cells comprising the expression vectors encompassed herein. In certain additional embodiments, the vector comprises a nucleotide sequence comprising SEQ ID NO: 64 and/or SEQ ID NO: 65. In yet additional embodiments, the vector comprises a nucleotide sequence comprising SEQ ID NO: 64 and SEQ ID NO: 65. In yet further embodiments, the vector comprises a nucleotide sequence comprising SEQ ID NOs: 68 or 69. "Cells" or "host cells" are terms used interchangeably herein. It is understood that such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein.

As described above, the antibody and antigen-binding fragment of the invention bind the N2 epitope and can therefore be used for treating a number of inflammatory diseases and conditions that are triggered by binding of natural IgM antibodies. For instance, the antibodies or fragments thereof can be used to treat inflammatory diseases or conditions such as reperfusion injury, ischemia injury, stroke, autoimmune hemolytic anemia, idiopathic thrombocytopenic purpura, rheumatoid arthritis, celiac disease, hyper-IgG immunodeficiency, arteriosclerosis, coronary artery disease, sepsis, myocarditis, encephalitis, transplant rejection, hepatitis, thyroiditis (e.g., Hashimoto's thyroiditis, Graves disease), osteoporosis, polymyositis, dermatomyositis, drug- or chemotherapy-induced inflammation (e.g., drug or chemotherapy induced nephritis, endocarditis, nephritis), Type I diabetes, gout, dermatitis, alopecia greata, systemic lupus erythematosus, lichen sclerosis, ulcerative colitis, diabetic retinopathy, pelvic inflammatory disease, periodontal disease, arthritis, juvenile chronic arthritis (e.g., chronic iridocyclitis), psoriasis, osteoporosis, nephropathy in diabetes mellitus, asthma, pelvic inflammatory disease, chronic inflammatory liver disease, chronic inflammatory lung disease, lung fibrosis, liver fibrosis, rheumatoid arthritis, chronic inflammatory liver disease, chronic inflammatory lung disease, lung fibrosis, liver fibrosis, Crohn's disease, ulcerative colitis, burn injury (or thermal injury), and other acute and chronic inflammatory diseases of the Central Nervous System (CNS; e.g., multiple sclerosis), gastrointestinal system, the skin and associated structures, the immune system, the hepato-biliary system, or any site in the body where pathology can occur with an inflammatory component.

The invention encompasses methods of inhibiting the activation of an immune response to the N2 antigen in a subject by administering to a subject an antibody described herein. In a further aspect, the invention encompasses methods of treating an inflammatory disease or condition, for example, ischemia-reperfusion injury, in a subject comprising administering to the subject a pharmaceutical composition comprising an antibody or fragment of the invention.

An inflammatory condition such as reperfusion or ischemic injury can result following a naturally occurring episode, including, for example, a stroke or myocardial infarction. Reperfusion or ischemic injury can also occur during and/or following a surgical procedure. Exemplary surgical procedures that cause can cause injury include a vessel-corrective technique selected from the group consisting of angioplasty, stenting procedure, atherectomy, and bypass surgery. In an exemplary embodiment, reperfusion or ischemic injury occurs in a cardiovascular tissue, such as the heart.

Data obtained from animal studies can be used in formulating a range of dosage for use in humans. The dosage of an antibody is within a range of circulating concentrations that include the $ED_{50}$ with little or no toxicity. The dosage can vary within this range depending upon the dosage form employed and the route of administration. For an antibody or fragment thereof used in the method described herein, the therapeutically effective dose can be estimated initially from in vitro assays. A dose can be formulated in animal models to achieve a circulating plasma concentration range that includes the $IC_{50}$ (i.e., the concentration of the test compound which achieves a half-maximal inhibition of symptoms) as determined in in vitro assay. This information can be used to more accurately determine useful doses in humans. Levels in plasma may be measured, for example, using enzyme linked immunosorbent assay (ELISA).

In some embodiments, an antibody or fragment thereof can be administered prior to, contemporaneously with, or subsequent to a tissue injury. In some embodiments, the pharmaceutical composition can be administered a few hours, a few days or a few weeks after tissue injury. In some embodiments, an antibody or fragment thereof can be administered prior to tissue injury, for example, in subjects at risk for reperfuion injury such as those patients that are about to undergo surgery. In additional embodiments, the antibody or fragment thereof can be administered.

A "therapeutically effective amount" or an "effective amount" is an amount which, alone or in combination with one or more other active agents, can control, decrease, inhibit, ameliorate, prevent or otherwise affect and/or achieve a recited effect. An effective amount of the agent to be administered can be determined using methods well-known in the art. One of skill in the art would take into account the mode of administration, the disease or condition (if any) being treated and the characteristics of the subject, such as general health, other diseases, age, sex, genotype, body weight and tolerance to drugs. A "patient" can refer to a human subject in need of treatment.

The antibody or fragment of the present invention can be provided in pharmaceutically acceptable carriers or formulated for a variety of modes of administration, including systemic and topical or localized administration. Techniques and formulations generally may be found in Remmington's Pharmaceutical Sciences, Meade Publishing Co., Easton, Pa. In certain embodiments, the antibody or fragment thereof is provided for transmucosal or transdermal delivery. For such administration, penetrants appropriate to the barrier to be permeated are used in the formulation with the polypeptide. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, compositions of the invention are formulated into ointments, salves, gels, or creams as generally known in the art.

The pharmaceutical compositions according to the invention are prepared by bringing an antibody or fragment thereof into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include, for example, antimicrobial, anti-oxidants, chelating agents and inert gases. Other pharmaceutically acceptable carriers include aqueous solutions, non-toxic excipients, including salts, preservatives, buffers and the like, as described, for instance, in The Science and Practice of Pharmacy, 20th Edition (Philadelphia College of Pharmacy and Science, 2000) and Remington: The Science and Practice of Pharmacy, 22nd Edition (Pharmaceutical Press and Philadelphia College of Pharmacy at University of the Sciences, 2012), and Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of each of which are hereby incorporated by reference. The pH and exact concentration of the various components of the pharmaceutical composition are adjusted according to routine skills in the art. See Goodman and Gilman's *The Pharmacological Basis for Therapeutics* (7th ed.) and Goodman and Gilman's *The Pharmacological Basis for Therapeutics,* 12th edition, (McGraw Hill Professional Publishing, 2010).

The pharmaceutical compositions can be prepared and administered in dose units. Solid dose units are tablets, capsules and suppositories and including, for example, alginate based pH dependent release gel caps. For treatment of a subject, depending on activity of the pharmaceutical composition, the manner of administration, nature and severity of the disorder, age and body weight of the subject, different daily doses are necessary. Under certain circumstances, however, higher or lower daily doses can be appropriate. The administration of the daily dose can be carried out both by single administration in the form of an individual dose unit or by several smaller dose units and also by multiple administrations of subdivided doses at specific intervals.

The pharmaceutical compositions according to the invention can be administered locally or systemically in a therapeutically effective dose. Amounts effective for this use will, of course, depend on the severity of the disease and the weight and general state of the subject. As discussed above, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249: 1527, (1990); Goodman and Gilman's *The Pharmacological Basis for Therapeutics,* 12th edition, (McGraw Hill Professional Publishing, 2010); each of which is herein incorporated by reference.

In one embodiment, the invention provides a pharmaceutical composition useful for administering an antibody or antigen-binding fragment thereof to a subject in need of such treatment. "Administering" the pharmaceutical composition of the invention may be accomplished by any means known to the skilled artisan. A "subject" refers to a mammal, most preferably a human.

The antibody or fragment thereof can be administered parenterally, enterically, by injection, rapid infusion, nasopharyngeal absorption, dermal absorption, rectally and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water. Where the disease or disorder is a gastrointestinal disorder oral formulations or suppository formulations are preferred.

Sterile injectable solutions can be prepared by incorporating an antibody or antigen-binding fragment thereof in the required amount (e.g., about 10 μg to about 10 mg/kg) in an appropriate solvent and then sterilizing, such as by sterile filtration. Further, powders can be prepared by standard techniques such as freeze drying or vacuum drying.

In another embodiment, antibody or fragment thereof is prepared with a biodegradable carrier for sustained release characteristics for either sustained release in the GI tract or for target organ implantation with long term active agent release characteristics to the intended site of activity. Biodegradable polymers include, for example, ethylene vinyl acetate, polyanhydrides, polyglycolic acids, polylactic acids, collagen, polyorthoesters, and poly acetic acid. Liposomal formulation can also be used.

Any route of administration compatible with the active principle can be used. In some embodiments, the route of administration is parenteral administration, such as subcutaneous, intramuscular or intravenous injection. The dose of the antibody or antigen-binding fragment thereof to be administered depends on the basis of the medical prescriptions according to age, weight and the individual response of the patient.

The daily non-weighted dosage for the patient can be between about 2.5-5.0 mg/Kg, e.g., about 2.5-3.0 mg/Kg, about 3.0-3.5 mg/Kg, about 3.5-4.0 mg/Kg, about 4.0-4.5 mg/Kg, and about 4.5-5.0 mg/Kg.

The pharmaceutical composition for parenteral administration can be prepared in an injectable form comprising the active principle and a suitable vehicle. Vehicles for the parenteral administration are well known in the art and comprise, for example, water, saline solution, Ringer solution and/or dextrose. The vehicle can contain small amounts of excipients in order to maintain the stability and isotonicity of the pharmaceutical preparation. The preparation of the cited solutions can be carried out according to the ordinary modalities.

The present invention has been described with reference to the specific embodiments, but the content of the description comprises all modifications and substitutions, including conservative amino acid substitutions, which can be brought by a person skilled in the art without extending beyond the meaning and purpose of the claims. The compositions can, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least about 30%, preferably at least about 40%, more preferably at least about 50%, about 60%, and even more preferably at least about 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences and the percent homology between two sequences is a function of the number of conserved positions shared by the sequences, taking into account the number of gaps, and the length of each gap, which need to be introduced for optimal alignment of the two sequences. The comparison of sequences and determination of percent identity and/or homology between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GCG software package (available on the internet at the Accelrys website, more specifically at www.accclrys.com http://www.accelrvs.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available on the world wide web with the extension gcg.com), using a NWSgapdna CMP matrix and a gap weight of 40, 50, 60, 70; or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frame shift gap penalty of 5.

The percent identity and/or homology between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

"Stringency hybridization" or "hybridizes under low stringency, medium stringency, high stringency, or very high stringency conditions" is used herein to describe conditions for hybridization and washing. Guidance for performing hybridization reactions can be found in Current Protocols in Molecular Biology, John Wiley & Sons, N.Y. (1989), 6.3.1-6:3.6, which is incorporated by reference. Aqueous and non-aqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. Calculations of homology or sequence identity between sequences (the terms are used interchangeably herein) are performed as described above.

The amino acid sequences referred to in the present application are listed below with the corresponding sequence identifier (SEQ ID NO):

```
m21G6 VH
                                                  (SEQ ID NO: 1)
QVQLQQPGAELVKPGASVKLSCKASGYTFTSYYMYWVKQRPGQGLEWIGGINPSNG

GTNFNEKFKSKATLTVDKSSSTAYMQLSSLTSEDSAVYYCTRWGYDREWFAYWGQ

GTLVTVSA.

m21G6 VL
                                                  (SEQ ID NO: 2)
DIVMTQAAPSVPVTPGESVSISCRSSKSLLHSNGNTYLYWFLQRPGQSPQVLIYRMSN

LASGVPDRFSGSGSGTAFTLRISRVEAEDVGVYYCMQHLEYPFTFGSGTKLEIKR.

VH CDR1
                                                  (SEQ ID NO: 3)
SYYMY.

VH CDR2
                                                  (SEQ ID NO: 4)
GINPSNGGTNFNEKFKS.

VH CDR3
                                                  (SEQ ID NO: 5)
GYDREWFAY.

VL CDR1
                                                  (SEQ ID NO: 6)
RSSKSLLHSNGNTYLY.

VL CDR2
                                                  (SEQ ID NO: 7)
RMSNLAS.

VL CDR3
                                                  (SEQ ID NO: 8)
MQHLEYPFT.
```

H1-21G6 Vh
(SEQ ID NO: 9)
QVQLVQSGAEVVKPGASVKLSCKASGYTFT<u>SYYMY</u>WVKQAPGQGLEWIG<u>GINPSNG</u>
<u>GTNFNEKFKS</u>KATLTVDKSASTAYMELSSLRSEDTAVYYCTR<u>WGYDREWFAY</u>WGQ
GTLVTVSS.

H2-21G6 Vh
(SEQ ID NO: 10)
QVQLVQSGAEVKKPGASVKVSCKASGYTFT<u>SYYMY</u>WVRQAPGQGLEWIG<u>GINPSN</u>
<u>GGTNFNEKFKS</u>KATMTVDKSTSTAYMELRSLRSDDSAVYYCTR<u>WGYDREWFAY</u>WG
QGTLVTVSS.

H3-21G6 Vh
(SEQ ID NO: 11)
QVQLVQSGAEVKKPGSSVKVSCKASGYTFT<u>SYYMY</u>WVRQAPGQGLEWIG<u>GINPSNG</u>
<u>GTNFNEKFKS</u>KATITVDKSTSTAYMELSSLRSEDTAVYYCTR<u>WGYDREWFAY</u>WGQG
TLVTVSS.

H4-21G6 Vh
(SEQ ID NO: 49)
QVQLVQSGAEVKKPGASVKVSCKASGYTFT<u>SYYMY</u>WVRQAPGQGLEWMG<u>GINPSN</u>
<u>GGTNFNEKFKS</u>RVTMTTDTSTSTAYMELRSLRSDDTAVYYCTR<u>WGYDREWFAY</u>WG
QGTLVTVSS.

L1-21G6 Vl (PopVk, CLL)
(SEQ ID NO: 12)
DIVMTQSPATLSVSPGERATISC<u>RSSKSLLHSNGNTYLY</u>WFQQKPGQPPKVLIY<u>RMSN</u>
<u>LAS</u>GVPARFSGSGSGTDFTLTISSVEPEDFATYYC<u>MQHLEYPFT</u>FGGGTKLEIKR.

L2-21G6 Vl
(SEQ ID NO: 13)
DIVMTQSPLSLPVTPGEPASISC<u>RSSKSLLHSNGNTYLY</u>WFLQKPGQSPQLLIY<u>RMSNL</u>
<u>AS</u>GVPDRFSGSGSGTDFTLKISRVEAEDVGVYYC<u>MQHLEYPFT</u>FGQGTKLEIKR.

L3-m21G6 Vl
(SEQ ID NO: 14)
DIVMTQTPLSLSYTPGQPASISC<u>RSSKSLLHSNGNTYLY</u>WFLQKPGQSPQLLIY<u>RMSNL</u>
<u>AS</u>GVPDRFSGSGSGTDFTLKISRVEAEDVGVYYC<u>MQHLEYPFT</u>FGQGTKLEIKR.

H1 VH FWR1
(SEQ ID NO: 15)
QVQLVQSGAEVVKPGASVKLSCKASGYTFT.

H1 VH FWR2
(SEQ ID NO: 16)
WVKQAPGQGLEWIG.

H1 VH FWR3
(SEQ ID NO: 17)
KATLTVDKSASTAYMELSSLRSEDTAVYYCTR.

H1 VH FWR4
(SEQ ID NO: 18)
WGQGTLVTVSS.

H2 VH FWR1
(SEQ ID NO: 19)
QVQLVQSGAEVKKPGASVKVSCKASGYTFT.

H2 VH FWR2
(SEQ ID NO: 20)
WVRQAPGQGLEWIG.

H2 VH FWR3
(SEQ ID NO: 21)
KATMTVDKSTSTAYMELRSLRSDDSAVYYCTR.

-continued

```
H2 VH FWR4
                                              (SEQ ID NO: 22)
WGQGTLVTVSS.

H3 VH FWR1
                                              (SEQ ID NO: 23)
QVQLVQSGAEVKKPGSSVKVSCKASGYTFT.

H3 VH FWR2
                                              (SEQ ID NO: 24)
WVRQAPGQGLEWIG.

H3 VH FWR3
                                              (SEQ ID NO: 25)
KATITVDKSTSTAYMELSSLRSEDTAVYYCTR.

H3 VH FWR4
                                              (SEQ ID NO: 26)
WGQGTLVTVSS.

H4 VH FWR1
                                              (SEQ ID NO: 19)
QVQLVQSGAEVKKPGASVKVSCKASGYTFT

H4 VH FWR2
                                              (SEQ ID NO: 50)
WVRQAPGQGLEWMG.

H4 VH FWR3
                                              (SEQ ID NO: 51)
RVTMTTDTSTSTAYMELRSLRSDDTAVYYCTR.

H4 VH FWR4
                                              (SEQ ID NO: 22)
WGQGTLVTVSS.

L1 VL FWR1
                                              (SEQ ID NO: 27)
DIVMTQSPATLSVSPGERATISC.

L1 VL FWR2
                                              (SEQ ID NO: 28)
WFQQKPGQPPKVLIY.

L1 VL FWR3
                                              (SEQ ID NO: 29)
GVPARFSGSGSGTDFTLTISSVEPEDFATYYC.

L1 VL FWR4
                                              (SEQ ID NO: 30)
FGGGTKLEIKR.

L2 VL FWR1
                                              (SEQ ID NO: 31)
DIVMTQSPLSLPVTPGEPASISC.

L2 VL FWR2
                                              (SEQ ID NO: 32)
WFLQKPGQSPQLLIY.

L2 VL FWR3
                                              (SEQ ID NO: 33)
GVPDRFSGSGSGTDFTLKISRVEAEDVGVYYC.

L2 VL FWR4
                                              (SEQ ID NO: 34)
FGQGTKLEIKR.

L3 VL FWR1
                                              (SEQ ID NO: 35)
DIVMTQTPLSLSYTPGQPASISC.

L3 VL FWR2
                                              (SEQ ID NO: 36)
WFLQKPGQSPQLLIY.

L3 VL FWR3
                                              (SEQ ID NO: 37)
GVPDRFSGSGSGTDFTLKISRVEAEDVGVYYC.
```

-continued

L3 VL FWR4
(SEQ ID NO: 38)
FGQGTKLEIKR.

H1 VH FWR3 with amino acid mutation to alanine
(SEQ ID NO: 39)
KATLTVDKSASTAYMELSSLRSEDTAVYYCAR.

H2 VH FWR3 with amino acid mutation to alanine
(SEQ ID NO: 40)
KATMTVDKSTSTAYMELRSLRSDDSAVYYCAR.

H3 VH FWR3 with amino acid mutation to alanine
(SEQ ID NO: 41)
KATITVDKSTSTAYMELSSLRSEDTAVYYCAR.

H4 VH FWR3
(SEQ ID NO: 52)
RVTMTTDTSTSTAYMELRSLRSDDTAVYYCAR

Amino Acid Variant of H2 Vh
(SEQ ID NO: 42)
QVQLVQSGAEVKKPGASLKVSCKASGYTFTSYYMYWVRQAPGQGLEWIGGINPSNG
GTNFNEKFKGRVTITRDKSTSTAYMELRSLRSEDSAVYYCARWGYDREWFAYWGQ
GTLVTVSS.

H1 VH with amino acid mutation to alanine in FWR3
(SEQ ID NO: 43)
QVQLVQSGAEVVKKPGASVKLSCKASGYTFT<u>SYYMY</u>WVKQAPGQGLEWIG<u>GINPSNG</u>
<u>GTNFNEKFKS</u>KATLTVDKSASTAYMELSSLRSEDTAVYYCAR<u>WGYDREWFAY</u>WGQ
GTLVTVSS.

H2 VH with amino acid mutation to alanine in FWR3
(SEQ ID NO: 44)
QVQLVQSGAEVKKPGASVKVSCKASGYTFT<u>SYYMY</u>WVRQAPGQGLEWIG<u>GINPSN</u>
<u>GGTNFNEKFKS</u>KATMTVDKSTSTAYMELRSLRSDDSAVYYCAR<u>WGYDREWFAY</u>W
GQGTLVTVSS.

H3 with amino acid mutation to alanine in FWR3
(SEQ ID NO: 45)
QVQLVQSGAEVKKPGSSVKVSCKASGYTFT<u>SYYMY</u>WVRQAPGQGLEWIG<u>GINPSNG</u>
<u>GTNFNEKFKS</u>KATITVDKSTSTAYMELSSLRSEDTAVYYCAR<u>WGYDREWFAY</u>WGQ
GTLVTVSS.

H4 VH with amino acid mutation to alanine in FWR3
(SEQ ID NO: 53)
QVQLVQSGAEVKKPGASVKVSCKASGYTFTSYYMYWVRQAPGQGLEWMGGINPSN
GGTNFNEKFKSRVTMTTDTSTSTAYMELRSLRSDDTAVYYCARWGYDREWFAYWG
QGTLVTVSS.

Amino Acid Variant of kappa chain (m21G6 V1)
(SEQ ID NO: 46)
EIVLTQSPGTLSLSPGERATLSCRASKSLLHSNGNTYLYWYQQKPGQAPRLLIYRMS
NRATGIPARFSGSGSGTDFTLTISSLEPEDFAVYYC MQHLEYPFTFGQGTKLEIKR.

N2 peptide
(SEQ ID NO: 47)
LMKNMDPLNDNV.

Peptide sequence
(SEQ ID NO: 48)
LMKNMDPLNDNI.

H4-21G6 Vh with leader sequence and the constant region of human IgG1
(SEQ ID NO: 54)
MGWSCIILFLVATATGVHSQVQLVQSGAEVKKPGASVKVSCKASGYTFTSYYMYWV
RQAPGQGLEWMGGINPSNGGTNFNEKFKSRVTMTTDTSTSTAYMELRSLRSDDTAV
YYCTRWGYDREWFAYWGQGTLVTVSSASTKGPSVFPLAPSSKSTSGGTAALGCLVK -continued

DYFPEPVTVSWNSGALTSGVHTFPAVLQSSGLYSLSSVVTVPSSSLGTQTYICNVNHK

PSNTKVDKRVEPKSCDKTHTCPPCPAPELLGGPSVFLFPPKPKDTLMISRTPEVTCVVV

DVSHEDPEVKFNWYVDGVEVHNAKTKPREEQYQSTYRVVSVLTVLHQDWLNGKEY

KCKVSNKALPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSVMHEALH

NHYTQKSLSLSPGK.

L2-21G6 Vl with leader sequence and the constant region of the
human kappa light chain
(SEQ ID NO: 55)
MGWSCIILFLVATATGVHGDIVMTQSPLSLPVTPGEPASISCRSSKSLLHSNGNTYLY

WFLQKPGQSPQLLIYRMSNLASGVPDRFSGSGSGTAFTLKISRVEAEDVGVYYCMQH

LEYPFTFGQGTKLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQGLSSPVT

KSFNRGEC.

Nucleotide sequence encoding H1-21G6 Vh
(SEQ ID NO: 56)
CAGGTCCAACTGGTGCAGtCTGGGGCTGAAGTGGTGAAGCCTGGGGCTTCAGTGA

AGTTGTCCTGCAAGGCTTCTGGCTACACCTTCACCAGCTACTATATGTACTGGGTG

AAGCAGGCGCCTGGACAAGGCCTTGAGTGGATTGGGGGGATTAATCCTAGCAAT

GGTGGTACTAACTTCAATGAGAAGTTCAAGAGCAAGGCCACACTGACTGTAGAC

AAATCCGCCAGCACAGCCTACATGGAACTCAGCAGCCTGAGATCTGAGGACACT

GCGGTCTATTACTGTACAAGATGGGGTTACGACAGGGAGTGGTTTGCTTACTGGG

GCCAAGGGACTCTGGTCACTGTCTCTTCA.

Nucleotide sequence encoding H2-21G6 Vh
(SEQ ID NO: 57)
CAGGTCCAACTGGTGCAGTCTGGGGCTGAAGTGAAGAAGCCTGGGGCTTCAGTG

AAGGTGTCCTGCAAGGCTTCTGGCTACACCTTCACCAGCTACTATATGTACTGGG

TGAGGCAGGCGCCTGGACAAGGCCTTGAGTGGATTGGGGGGATTAATCCTAGCA

ATGGTGGTACTAACTTCAATGAGAAGTTCAAGAGCAAGGCCACAATGACTGTAG

ACAAATCCACCAGCACAGCCTACATGGAACTCCGCAGCCTGAGATCTGACGACA

CTGCGGTCTATTACTGTACAAGATGGGGTTACGACAGGGAGTGGTTTGCTTACTG

GGGCCAAGGGACTCTGGTCACTGTCTCTTCA.

Nucleotide sequence encoding H3-21G6 Vh
(SEQ ID NO: 58)
CAGGTCCAACTGGTGCAGTCTGGGGCTGAAGTGAAGAAGCCTGGGTCTTCAGTGA

AGGTGTCCTGCAAGGCTTCTGGCTACACCTTCACCAGCTACTATATGTACTGGGT

GAGGCAGGCGCCTGGACAAGGCCTTGAGTGGATTGGGGGGATTAATCCTAGCAA

TGGTGGTACTAACTTCAATGAGAAGTTCAAGAGCAAGGCCACAATCACTGTAGAC

AAATCCACCAGCACAGCCTACATGGAACTCAGCAGcCTGAGATCTGAGGACACTG

CGGTCTATTACTGTACAAGATGGGGTTACGACAGGGAGTGGTTTGCTTACTGGGG

CCAAGGGACTCTGGTCACTGTCTCTTCA.

Nucloetide sequence encoding H4-21G6 Vh
(SEQ ID NO: 59)
CAGGTCCAACTGGTGCAGTCTGGGGCTGAAGTGAAGAAGCCTGGGGCTTCAGTG

AAGGTGTCCTGCAAGGCTTCTGGCTACACCTTCACCAGCTACTATATGTACTGGG

TGAGGCAGGCGCCTGGACAAGGCCTTGAGTGGATGGGGGGGATTAATCCTAGCA

-continued

ATGGTGGTACTAACTTCAATGAGAAGTTCAAGAGCAGGGTCACAATGACTACAG

ACACATCCACCAGCACAGCCTACATGGAACTCCGCAGCCTGAGATCTGACGACAC

TGCGGTCTATTACTGTACAAGATGGGGTTACGACAGGGAGTGGTTTGCTTACTGG

GGCCAAGGGACTCTGGTCACTGTCTCTTCA.

Optimized nucleotide sequence encoding H4-21G6 Vh including intron
from vector, leader sequence and IgG1 constant region
(SEQ ID NO: 60)
CACTATAGGGCGAATTGAAGGAAGGCCGTCAAGGCCGCATCCTAGGGCCACCAT

GGGCTGGTCCTGCATCATCCTGTTTCTGGTCGCCACCGCCACCGGCGTGCACTCCC

AGGTCCAGCTGGTCCAGTCTGGCGCCGAAGTGAAGAAACCTGGCGCCTCCGTGA

AGGTGTCCTGCAAGGCCTCCGGCTACACCTTCACCAGCTACTACATGTACTGGGT

CCGACAGGCCCCAGGCCAGGGACTGGAATGGATGGGCGGCATCAACCCCTCCAA

CGGCGGCACCAACTTCAACGAGAAGTTCAAGTCCAGAGTGACCATGACCACCGA

CACCTCCACCTCCACCGCCTACATGGAACTGCGGTCCCTGCGGAGCGACGACACC

GCCGTGTACTACTGCACCAGATGGGGCTACGACAGAGAGTGGTTCGCCTACTGGG

GCCAGGGCACCCTGGTCACAGTGTCCTCCGCTTCCACCAAGGGCCCCTCCGTGTT

CCCTCTGGCCCCCTCCAGCAAGTCCACCTCTGGCGGCACCGCTGCCCTGGGCTGC

CTGGTCAAAGACTACTTCCCCGAGCCCGTGACCGTGTCCTGGAACTCTGGCGCCC

TGACCAGCGGCGTGCACACCTTCCCTGCCGTGCTGCAGTCTTCCGGCCTGTACTCC

CTGTCCTCCGTGGTCACCGTGCCCTCCAGCTCTCTGGGCACCCAGACCTACATCTG

CAACGTGAACCACAAGCCCTCCAACACCAAGGTGGACAAGCGGGTGGAACCCAA

GTCCTGCGACAAGACCCACACCTGTCCCCCCTGCCCTGCCCCTGAACTGCTGGGC

GGACCTTCCGTGTTCCTGTTCCCCCCAAAGCCCAAGGACACCCTGATGATCTCCC

GGACCCCCGAAGTGACCTGCGTGGTGGTGGACGTGTCCCACGAGGACCCTGAAG

TGAAGTTCAATTGGTACGTGGACGGCGTGGAAGTGCACAACGCCAAGACCAAGC

CCAGAGAGGAACAGTACCAGTCCACCTACCGGGTGGTGTCTGTGCTGACCGTGCT

GCACCAGGACTGGCTGAACGGCAAAGAGTACAAGTGCAAGGTCTCCAACAAGGC

CCTGCCTGCCCCCATCGAAAAGACCATCTCCAAGGCCAAGGGCCAGCCCCGCGA

GCCCCAGGTGTACACACTGCCCCCTAGCCGGGAAGAGATGACCAAGAACCAGGT

GTCCCTGACCTGTCTGGTCAAAGGCTTCTACCCCTCCGACATTGCCGTGGAATGG

GAGTCCAACGGCCAGCCCGAGAACAACTACAAGACCACCCCCCCTGTGCTGGAC

TCCGACGGCTCATTCTTCCTGTACTCCAAGCTGACCGTGGACAAGTCCCGGTGGC

AGCAGGGCAACGTGTTCTCCTGCTCCGTGATGCACGAGGCCCTGCACAACCACTA

CACCCAGAAGTCCCTGTCCCTGAGCCCCGGCAAGTGATGAGTATACCTGGGCCTC

ATGGGCCTTCCTTTCACTGCCCGCTTTCCAG.

Nucleotide sequence encoding L1-21G6 Vl
(SEQ ID NO: 61)
GATATTGTGATGACTCAGTCTCCAGCCACTCTATCTGTCTCTCCTGGAGAGCGAGC

AACCATCTCCTGCAGGGCTAGTAAGAGTCTCCTGCATAGTAATGGCAACACTTAC

TTGTATTGGTTCCAGCAGAAGCCAGGCCAGCCTCCTAAGGTCCTGATATATCGGA

TGTCCAACCTTGCCTCAGGAGTCCCAGCCAGGTTCAGTGGCAGTGGGTCAGGAAC

TGATTTCACACTGACAATCAGTTCggtgGAGccTGAGGATTTTGCTACTTATTACTGT

```
ATGCAACATCTAGAATATCCATTCACGTTCGGCGGGGGGACAAAGTTGGAAATA

AAACG.
Nucleotide sequence encoding L2-21G6 V1
                                                   (SEQ ID NO: 62)
GATATTGTGATGACTCAGTCTCCACTCTCTCTACCTGTCACTCCTGGAGAGcCAGC

ATCCATCTCCTGCAGGTCTAGTAAGAGTCTCCTGCATAGTAATGGCAACACTTAC

TTGTATTGGTTCCTGCAGAAGCCAGGCCAGTCTCCTCAGcTCCTGATATATCGGAT

GTCCAACCTTGCCTCAGGAGTCCCAGACAGGTTCAGTGGCAGTGGGTCAGGAACT

GcTTTCACACTGAAAATCAGTAGAGTGGAGGCTGAGGATGTGGGTGTTTATTACT

GTATGCAACATCTAGAATATCCATTCACGTTCGGCCAGGGGACAAAGCTGGAAAT

AAAACG.
Nucleotide sequence encoding L3-21G6 V1
                                                   (SEQ ID NO: 63)
GATATTGTGATGACTCAGACTCCACTCTCTCTAtCTGTCACTCCTGGAcAGcCAGCA

TCCATCTCCTGCAGGTCTAGTAAGAGTCTCCTGCATAGTAATGGCAACACTTACTT

GTATTGGTTCCTGCAGAAGCCAGGCCAGTCTCCTCAGcTCCTGATATATCGGATGT

CCAACCTTGCCTCAGGAGTCCCAGACAGGTTCAGTGGCAGTGGGTCAGGAACTGa

TTTCACACTGAAAATCAGTAGAGTGGAGGCTGAGGATGTGGGTGTTTATTACTGT

ATGCAACATCTAGAATATCCATTCACGTTCGGCCAGGGGACAAAGCTGGAATA

AAACG.
Optimized nucleotide sequence encoding H4-21G6 Vh
                                                   (SEQ ID NO: 64)
CAGGTCCAGCTGGTCCAGTCTGGCGCCGAAGTGAAGAAACCTGGCGCCTCCGTGA

AGGTGTCCTGCAAGGCCTCCGGCTACACCTTCACCAGCTACTACATGTACTGGGT

CCGACAGGCCCCAGGCCAGGGACTGGAATGGATGGGCGGCATCAACCCCTCCAA

CGGCGGCACCAACTTCAACGAGAAGTTCAAGTCCAGAGTGACCATGACCACCGA

CACCTCCACCTCCACCGCCTACATGGAACTGCGGTCCCTGCGGAGCGACGACACC

GCCGTGTACTACTGCACCAGATGGGGCTACGACAGAGAGTGGTTCGCCTACTGGG

GCCAGGGCACCCTGGTCACAGTGTCCTCC.
Optimized nucleotide sequence encoding L2-21G6 VI
                                                   (SEQ ID NO: 65)
GACATCGTGATGACCCAGTCCCCCCTGTCCCTGCCCGTGACACCTGGCGAGCCTG

CCTCCATCTCCTGCCGGTCCTCCAAGTCCCTGCTGCACTCCAACGGCAATACCTAC

CTGTACTGGTTCCTGCAGAAGCCCGGCCAGTCCCCTCAGCTGCTGATCTACCGGA

TGTCCAACCTGGCCTCCGGCGTGCCCGACAGATTCTCCGGCTCTGGCTCTGGCAC

AGCCTTCACCCTGAAGATCTCCCGGGTGGAAGCCGAGGACGTGGGCGTGTACTAC

TGCATGCAGCACCTGGAATACCCCTTCACCTTCGGCCAGGGCACCAAGCTGGAAA

TCAAGCGG.
Nucleotide sequence encoding H4-21G6 Vh including leader
sequence and constant region
                                                   (SEQ ID NO: 66)
ATGGGATGGTCATGTATCATCCTTTTTCTAGTAGCAACTGCAACCGGTGTCCACTC

CCAGGTCCAACTGGTGCAGTCTGGGGCTGAAGTGAAGAAGCCTGGGGCTTCAGT

GAAGGTGTCCTGCAAGGCTTCTGGCTACACCTTCACCAGCTACTATATGTACTGG

GTGAGGCAGGCGCCTGGACAAGGCCTTGAGTGGATGGGGGGGATTAATCCTAGC

AATGGTGGTACTAACTTCAATGAGAAGTTCAAGAGCAGGGTCACAATGACTACA
```

-continued

```
GACACATCCACCAGCACAGCCTACATGGAACTCCGCAGCCTGAGATCTGACGAC

ACTGCGGTCTATTACTGTACAAGATGGGGTTACGACAGGGAGTGGTTTGCTTACT

GGGGCCAAGGGACTCTGGTCACTGTCTCTTCAGCGTCGACCAAGGGCCCATCGGT

CTTCCCCCTGGCACCCTCCTCCAAGAGCACCTCTGGGGGCACAGCGGCCCTGGGC

TGCCTGGTCAAGGACTACTTCCCCGAACCTGTGACGGTCTCGTGGAACTCAGGCG

CCCTGACCAGCGGCGTGCACACCTTCCCGGCTGTCCTACAGTCCTCAGGACTCTA

CTCCCTCAGCAGCGTGGTGACCGTGCCCTCCAGCAGCTTGGGCACCCAGACCTAC

ATCTGCAACGTGAATCACAAGCCCAGCAACACCAAGGTGGACAAGAGAGTTGAG

CCCAAATCTTGTGACAAAACTCACACATGCCCACCGTGCCCAGCACCTGAACTCC

TGGGGGGACCGTCAGTCTTCCTCTTCCCCCCAAAACCCAAGGACACCCTCATGAT

CTCCCGGACCCCTGAGGTCACATGCGTGGTGGTGGACGTGAGCCACGAAGACCCT

GAGGTCAAGTTCAACTGGTACGTGGACGGCGTGGAGGTGCATAATGCCAAGACA

AAGCCGCGGGAGGAGCAGTACCAGAGCACGTACCGTGTGGTCAGCGTCCTCACC

GTCCTGCACCAGGACTGGCTGAATGGCAAGGAGTACAAGTGCAAGGTCTCCAAC

AAAGCCCTCCCAGCCCCCATCGAGAAAACCATCTCCAAAGCCAAAGGGCAGCCC

CGAGAACCACAGGTGTACACCCTGCCCCCATCCCGGGAGGAGATGACCAAGAAC

CAGGTCAGCCTGACCTGCCTGGTCAAAGGCTTCTATCCCAGCGACATCGCCGTGG

AGTGGGAGAGCAATGGGCAGCCGGAGAACAACTACAAGACCACGCCTCCCGTGC

TGGACTCCGACGGCTCCTTCTTCCTCTATAGCAAGCTCACCGTGGACAAGAGCAG

GTGGCAGCAGGGGAACGTCTTCTCATGCTCCGTGATGCATGAGGCTCTGCACAAC

CACTACACGCAGAAGAGCCTCTCCCTGTCCCCGGGTAAATGA.
```

Nucleotide sequence encoding L2-21G6 V1 including leader sequence
and human kappa light chain (SEQ ID NO: 67)

```
ATGGGATGGTCATGTATCATCCTTTTTCTAGTAGCAACTGCAACCGGTGTACATG

GGGATATTGTGATGACTCAGTCTCCACTCTCTCTACCTGTCACTCCTGGAGAGCCA

GCATCCATCTCCTGCAGGTCTAGTAAGAGTCTCCTGCATAGTAATGGCAACACTT

ACTTGTATTGGTTCCTGCAGAAGCCAGGCCAGTCTCCTCAGCTCCTGATATATCGG

ATGTCCAACCTTGCCTCAGGAGTCCCAGACAGGTTCAGTGGCAGTGGGTCAGGAA

CTGCTTTCACACTGAAAATCAGTAGAGTGGAGGCTGAGGATGTGGGTGTTTATTA

CTGTATGCAACATCTAGAATATCCATTCACGTTCGGCCAGGGGACAAAGCTGGAA

ATAAAACGTACGGTGGCTGCACCATCTGTCTTCATCTTCCCGCCATCTGATGAGC

AGTTGAAATCTGGAACTGCCTCTGTTGTGTGCCTGCTGAATAACTTCTATCCCAGA

GAGGCCAAAGTACAGTGGAAGGTGGATAACGCCCTCCAATCGGGTAACTCCCAG

GAGAGTGTCACAGAGCAGGACAGCAAGGACAGCACCTACAGCCTCAGCAGCACC

CTGACGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGAGTGT

TAG.
```

Optimized nucleotide sequence encoding H4-21G6 Vh with leader
sequence and IgG1 constant region (SEQ ID NO: 68)

```
ATGGGCTGGTCCTGCATCATCCTGTTTCTGGTCGCCACCGCCACCGGCGTGCACTC

CCAGGTCCAGCTGGTCCAGTCTGGCGCCGAAGTGAAGAAACCTGGCGCCTCCGTG
```

-continued

```
AAGGTGTCCTGCAAGGCCTCCGGCTACACCTTCACCAGCTACTACATGTACTGGG

TCCGACAGGCCCCAGGCCAGGGACTGGAATGGATGGGCGGCATCAACCCCTCCA

ACGGCGGCACCAACTTCAACGAGAAGTTCAAGTCCAGAGTGACCATGACCACCG

ACACCTCCACCTCCACCGCCTACATGGAACTGCGGTCCCTGCGGAGCGACGACAC

CGCCGTGTACTACTGCACCAGATGGGGCTACGACAGAGAGTGGTTCGCCTACTGG

GGCCAGGGCACCCTGGTCACAGTGTCCTCCGCTTCCACCAAGGGCCCCTCCGTGT

TCCCTCTGGCCCCCTCCAGCAAGTCCACCTCTGGCGGCACCGCTGCCCTGGGCTG

CCTGGTCAAAGACTACTTCCCCGAGCCCGTGACCGTGTCCTGGAACTCTGGCGCC

CTGACCAGCGGCGTGCACACCTTCCCTGCCGTGCTGCAGTCTTCCGGCCTGTACTC

CCTGTCCTCCGTGGTCACCGTGCCCTCCAGCTCTCTGGGCACCCAGACCTACATCT

GCAACGTGAACCACAAGCCCTCCAACACCAAGGTGGACAAGCGGGTGGAACCCA

AGTCCTGCGACAAGACCCACACCTGTCCCCCCTGCCCTGCCCCTGAACTGCTGGG

CGGACCTTCCGTGTTCCTGTTCCCCCCAAAGCCCAAGGACACCCTGATGATCTCCC

GGACCCCCGAAGTGACCTGCGTGGTGGTGGACGTGTCCCACGAGGACCCTGAAG

TGAAGTTCAATTGGTACGTGGACGGCGTGGAAGTGCACAACGCCAAGACCAAGC

CCAGAGAGGAACAGTACCAGTCCACCTACCGGGTGGTGTCTGTGCTGACCGTGCT

GCACCAGGACTGGCTGAACGGCAAAGAGTACAAGTGCAAGGTCTCCAACAAGGC

CCTGCCTGCCCCCATCGAAAAGACCATCTCCAAGGCCAAGGGCCAGCCCCGCGA

GCCCCAGGTGTACACACTGCCCCCTAGCCGGGAAGAGATGACCAAGAACCAGGT

GTCCCTGACCTGTCTGGTCAAAGGCTTCTACCCCTCCGACATTGCCGTGGAATGG

GAGTCCAACGGCCAGCCCGAGAACAACTACAAGACCACCCCCCCTGTGCTGGAC

TCCGACGGCTCATTCTTCCTGTACTCCAAGCTGACCGTGGACAAGTCCCGGTGGC

AGCAGGGCAACGTGTTCTCCTGCTCCGTGATGCACGAGGCCCTGCACAACCACTA

CACCCAGAAGTCCCTGTCCCTGAGCCCCGGCAAGTGATGAGTATACCTGGGCCTC

ATGGGCCTTCCTTTCACTGCCCGCTTTCCAG.
```

Optimized nucleotide sequence encoding L2-21G6 V1 including leader sequence and human kappa light chain (SEQ ID NO: 69)

```
CGAATTGGCGGAAGGCCGTCAAGGCCACGTGTCTTGTCCAGAGCTCGATATCGCC

ACCATGGGCTGGTCCTGCATCATCCTGTTTCTGGTCGCCACCGCCACCGGCGTGC

ACGGCGACATCGTGATGACCCAGTCCCCCCTGTCCCTGCCCGTGACACCTGGCGA

GCCTGCCTCCATCTCCTGCCGGTCCTCCAAGTCCCTGCTGCACTCCAACGGCAATA

CCTACCTGTACTGGTTCCTGCAGAAGCCCGGCCAGTCCCCTCAGCTGCTGATCTAC

CGGATGTCCAACCTGGCCTCCGGCGTGCCCGACAGATTCTCCGGCTCTGGCTCTG

GCACAGCCTTCACCCTGAAGATCTCCCGGGTGGAAGCCGAGGACGTGGGCGTGT

ACTACTGCATGCAGCACCTGGAATACCCCTTCACCTTCGGCCAGGGCACCAAGCT

GGAAATCAAGCGGACCGTGGCCGCTCCCTCCGTGTTCATCTTCCCACCCTCCGAC

GAGCAGCTGAAGTCCGGCACCGCCTCCGTCGTCTGCCTGCTGAACAACTTCTACC

CCCGCGAGGCCAAGGTGCAGTGGAAGGTGGACAACGCCCTGCAGTCCGGCAACT

CCCAGGAATCCGTCACCGAGCAGGACTCCAAGGACAGCACCTACTCCCTGTCTTC

CACCCTGACCCTGTCCAAGGCCGACTACGAGAAGCACAAGGTGTACGCCTGCGA

AGTGACCCACCAGGGCCTGTCCAGCCCCGTGACCAAGTCCTTCAACCGGGGCGAG
```

```
-continued
TGCTGATGATTAATTAAGGTACCTGGAGCACAAGACTGGCCTCATGGGCCTTCCG
CTCACTGC.
```

The invention is illustrated by the following non-limiting examples.

EXEMPLIFICATION

Example 1

Humanization of Murine Antibody 21G6

Murine 21G6 is an IgG1 heavy chain and kappa light chain that was raised against the non-muscle myosin neo-epitope N2 12mer sequence: LMKNMDPLNDNV (SEQ ID No: 47). The murine 21G6 antibody is described in more detail in U.S. Pat. No. 8,324,352, the contents of which are expressly incorporated herein. Using the IMGT database (www.imgt.org), a search was performed to identify the human germline antibody sequences with the greatest homology to the murine 21G6 antibody. In addition, a BLAST search was performed to identify homologous human non-germline antibodies. The sequences shown in FIG. 1 were determined to have the highest amino acid homology.

FIG. 1 shows a sequence comparison for the murine 21G6 heavy chain variable (VH) region variable heavy and the humanized heavy chain variable regions (VH) H1-21G6, H2-21G6 and H3-21G6 and also shows a sequence comparison of the murine 21G6 light chain variable (VL) region and the humanized light chain variable regions light chain (VL) regions L1-21G6, L2-21G6 and L3-21G6.

The H1-21G6 and L1-21G6 frameworks were derived from B-cells obtained from lupus and chronic lymphocytic leukemia (CLL) patients for the heavy and light chains, respectively. The remaining sequences represent the germline sequences with the highest homology that encode productive antibody. All of the humanized sequences maintain the murine 21G6 CDR regions which are shown inside the boxes in FIG. 1. The humanized variable regions were cloned into a vector containing wild type human IgG1, human IgG1 containing a mutation at amino acid 297 (Asn 297 to Q297), human IgG4 containing a mutation at amino acid 228 (serine to proline) and human kappa light chain. Each antibody (heavy and light) combination was expressed by transient co-transfection in 293A cells (in the presence of low Ig serum). The antibody containing supernatants were collected and analyzed for binding to the N2 peptide by ELISA and BIACORE™ ×100 system. All experiments were performed using a BIACORE™ ×100 system. For antibody capture experiments, a CM5 chip was prepared by 10 ul/minute injection of EDC/NHS (N-ethyl-N'-(3-dimethylaminopropyl) carbodiimide (EDC), N-hydroxysuccinimide (NHS) for 7 minutes, followed by a 10 ul/minute injection of anti-human Fc (GE Lifesciences) at a concentration of 25ug/ml in sodium acetate at pH 5 for 3 minutes. Ethanolamine-HCl was injected for 7 minutes at 10 ul/minute. The chimeric or humanized antibodies were captured onto flow cell 2 and N2 peptide at varying concentrations was flowed over flow cells 1 and 2 at a rate of 30ul/minute with a contact time of 120 seconds and a dissociation period of 120 seconds. Complete removal of captured antibody was accomplished by regeneration with 3M MgC12 for 30 seconds at a flow rate of 10ul/minute. For peptide immobilized experiments, a CM5 chip was prepared by 10ul/minute injection of EDC/NHS (N-ethyl-N'-(3-dimethylaminopropyl) carbodiimide (EDC), N-hydroxysuccinimide (NHS) for 7 minutes, followed by a 10ul/minute injection of NEUTRAVIDIN® protein (ThermoFisher Pierce) at a concentration of 5ug/ml in sodium acetate, pH 5 to an immobilization response of 100-200RU. Ethanolamine-HCl was injected for 7 minutes at 10ul/minute. Biotin-labeled N2 peptide was captured on flow channel 2 with the goal of an experimental Rmax of about 50-100RU. Purified chimeric or humanized antibodies were flowed over both flow channels at a rate of 30ul/min for a contact time of 120 seconds and allowed to dissociate for 600 seconds. Regeneration was achieved with glycine pH 1.7 for 30 seconds thus retaining an active surface. The apparent affinity constants and antibody on/off rates are shown in Tables 1A, 1B, 2, 3A and 3B below:

TABLE 1A

Apparent Affinity Constants for variable regions and wild type human IgG1 heavy chain (Immobilized Antibody, N2 peptide in solution)

| Heavy Chain | Light Chain | Kd (uM) by IgG capture |
|---|---|---|
| H1 | L2 | 17 |
| H1 | L3 | 20.9 |
| H1 | L1 | 6.6-7.7 |
| H1 | L2 | 6.4-8.4 |
| H2 | L3 | 9.56 |
| H2 | L1 | 9.8-11 |
| H3 | L2 | 11.5 |
| H3 | L3 | 9.38 |
| H3 | L1 | 7-9 |
| m21G6 | m21G6 | 4-6 |
| CHIgG1 (human heavy chain constant region IgG1) | Ch | 6-7 |
| CHIgG4 (human heavy chain constant region IgG4) | Ch | 4.1 |

TABLE 1B

Apparent Affinity Constants for variable regions and human IgG1 heavy chain with mutation at position 297 from Asn to Gln (Immobilized Antibody, N2 peptide in solution)

| Heavy Chain (N297Q) | Light Chain | Kd (uM) by IgG capture |
|---|---|---|
| H1 | L2 | TBD |
| H1 | L3 | TBD |
| H1 | L1 | 9 |
| H2 | L2 | 3.1-3.7 |
| H2 | L3 | 8.8 |
| H2 | L1 | TBD |
| H3 | L2 | TBD |
| H3 | L1 | 20 |
| H3 | L3 | TBD |
| CHIgG1 (human heavy chain constant region IgG1) | CH | 5.6 |

(TBD indicated "to be determined")

TABLE 2

Antibody on- and off-rates (immobilized N2, antibody in solution)

| Heavy Chain | Light Chain | Ka (e + 4) (on-rate) | kd (e − 3) (off-rate) | Affinity (nM) kd/ka (monovalent) | Steady state affinity (nM) |
|---|---|---|---|---|---|
| H1 | L3 | 0.63 | 9.93 | 1580 | 1000 |
| H1 | L1 | 1.5-4.3 | 4.3-6-5 | 100-430 | 320 |
| H2 | L2 | 2.0-3.2 | 8.6-9.1 | 280-420 | 240 |
| H2 | L3 | 2.4 | 3.5 | 140 | 680 |
| H2 | L1 | 0.7 | 4.63 | 660 | NA |
| H3 | L2 | 1.2 | 7.2 | 640 | NA |
| H3 | L3 | 0.60 | 5.61 | 900 | NA |
| H3 | L1 | 2.0-5.2 | 3-6.5 | 300 | 280 |
| ch21G6 N297Q (human heavy chain constant region IgG1 with Q297 mutation) | ch21G6 | 7-10 | 7-19 | 100-200 | 196-240 |
| ch21G6 IgG4 (human heavy chain constant region IgG4) | ch21G6 | 5 | 40 | 800 | 113 |
| m21G6 | m21G6 | 1-11 | 5-53 | 200-400 | 313-540 |

TABLE 3A

Apparent Affinity Constant for variable region H4 and IgG1 heavy chain with mutation at position 297 from Asn to Gln (Immobilized Antibody, N2 peptide in solution)

| Heavy Chain (N297Q) | Light Chain | Kd (uM) by IgG capture and direct immobilization |
|---|---|---|
| H4 | L2 | 6-11 |

TABLE 3B

Antibody on- and off-rates (immobilized N2, antibody in solution)

| Heavy Chain | Light Chain | Ka (e + 4) (on-rate) | kd (e − 3) (off-rate) | Affinity (nM) kd/ka (monovalent) | Steady state affinity (nM) |
|---|---|---|---|---|---|
| H4 | L2 | 2 | 2 | 100 | TBD |

As determined by t-test, there was no significant difference between murine 21G6 and H1/L1 and murine 21G6 and H2/L2. (Murine 21G6: n=4; 9r/9r: n=3; 69/9r: n=2).

Example 2

Optimization of Nucleotide Sequences for Increased Production in CHO Cells

Optimization was performed in order to use codon preferences of Cricetulus griseus (Chinese hamster) for optimal expression of the humanized antibody. The GENEOPTIMIZER® program also optimized sequence to prevent aberrant mRNA splicing, eliminate undesirable polyA binding motifs, optimize GC content of the gene and prevent unwanted secondary RNA structures that might decrease protein translation efficiency, thereby increasing overall antibody expression. Amino acid and nucleotides sequences for H4-21G6 and L2-21G6 (SEQ ID NOs: 54, 66, 55 and 67, respectively) were sent to Life Technologies for optimization using the GENEOPTIMIZER® Process described at www.lifetechnologies.com/us/en/home/life-science/cloning/gene-synthesis/geneart-gene-synthesis/geneoptimizer.html (the contents of which are expressly incorporated by reference herein). FIG. 3 shows a nucleotide sequence encoding the humanized heavy chain variable region H4 that was optimized for the production of the humanized antibody in Chinese hamster ovary (CHO) cells where each + indicates where a change was made as compared to SEQ ID NO: 66. FIG. 4 shows a nucleotide sequence encoding the humanized light chain variable region L2 that was optimized for the production of the humanized antibody in Chinese hamster ovary (CHO) cells. Each + indicates where a change was made as compared to SEQ ID NO: 67. FIG. 5 depicts the levels of recombinant antibody expression on day 5 post-transfection with either native (red) or optimized (blue) antibody sequences. Incorporation of the recombinant antibody sequence into the CHO cells was accomplished by selection in the presence of 10ug/ml puromycin and 100mM methotrexate for transfectants DS5 and DS7 or 20ug/ml puromycin and 200mM methotrexate for transfectants DS6 and DS8.

While this invention has been particularly shown and described with references to preferred embodiments thereof, it will be understood by those skilled in the art that various changes in form and details may be made therein without departing from the scope of the invention encompassed by the appended claims.

What is claimed is:

1. A humanized, anti-N2 antibody or antigen-binding fragment thereof, comprising a heavy chain variable (VH) region and a light chain variable (VL) region, wherein the VH region comprises the sequence of SEQ ID NO: 49 and wherein the VL region comprises the sequence of SEQ ID NO: 13.

2. The antibody or antigen-binding fragment of claim 1, wherein the VH region consists of the amino acid sequence of SEQ ID NO: 49 and the VL region consists of the amino acid sequence of SEQ ID NO: 13.

3. The antibody or antigen-binding fragment of claim 1, wherein the VH region consists of the amino acid sequence of SEQ ID NO: 54 and the VL region consists of the sequence of SEQ ID NO: 13.

4. The antibody or antigen-binding fragment of claim 1, wherein the isotype of the constant region is IgG1, IgG2, IgG3, or IgG4.

5. The antibody or antigen-binding fragment of claim 4, wherein the isotype of the IgG constant region is IgG1.

6. The antibody or antigen-binding fragment of claim 4, wherein the isotype of the IgG constant region is IgG4.

7. The antibody or antigen-binding fragment of claim 1, having a heavy chain immunoglobulin constant domain selected from the group consisting of a human IgG1 constant domain and a human IgG4 constant domain.

8. The antibody or antigen-binding fragment of claim 1, having a human Ig kappa constant domain.

9. The antibody or antigen-binding fragment of claim 1, wherein the antibody is aglycosylated.

10. The antibody or antigen-binding fragment of claim 1, having a human IgG1 constant domain that is aglycosylated by replacing the amino acid corresponding to asparagine (Asn) 297 of the constant region heavy chain with an alternative amino acid residue.

11. The antibody or antigen-binding fragment of claim 10, wherein the Asn 297 is replaced with glutamine, alanine, histidine or glycine.

12. The antibody or antigen-binding fragment of claim 11, wherein the Asn 297 is replaced with glutamine.

13. The antibody or antigen-binding fragment of claim 1, wherein the heavy chain immunoglobulin constant domain is a human IgG4 constant domain wherein serine 228 is replaced with proline.

14. The antibody or antigen-binding fragment of claim 1, which is a scFv, diabody, Fab, minibody or scFv-Fc.

15. A pharmaceutical composition comprising a pharmaceutically acceptable carrier and an antibody or antigen-binding fragment of claim 1.

16. A method comprising administering the antibody or antigen-binding fragment of claim 1 to a subject with an inflammatory disease or disorder.

17. The method of claim 16, wherein the inflammatory disease or disorder is ischemia-reperfusion injury.

18. The method of claim 16, wherein the subject is a mammal.

19. The method of claim 18, wherein the mammal is a human.

20. The method of claim 16, wherein the ischemia-reperfusion results after myocardial infarction, stroke or a surgical procedure.

* * * * *

SEQUENCE LISTING

```
<160> NUMBER OF SEQ ID NOS: 69

<210> SEQ ID NO 1
<211> LENGTH: 119
<212> TYPE: PRT
<213> ORGANISM: Mus sp.

<400> SEQUENCE: 1

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Met Tyr Trp Val Lys Gln Arg Pro Gly Gln Gly Leu Glu Trp Ile
        35                  40                  45

Gly Gly Ile Asn Pro Ser Asn Gly Gly Thr Asn Phe Asn Glu Lys Phe
```

```
                    50                  55                  60
Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                     85                  90                  95

Thr Arg Trp Gly Tyr Asp Arg Glu Trp Phe Ala Tyr Trp Gly Gln Gly
                100                 105                 110

Thr Leu Val Thr Val Ser Ala
            115

<210> SEQ ID NO 2
<211> LENGTH: 113
<212> TYPE: PRT
<213> ORGANISM: Mus sp.

<400> SEQUENCE: 2

Asp Ile Val Met Thr Gln Ala Ala Pro Ser Val Pro Val Thr Pro Gly
 1               5                  10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
             35                  40                  45

Pro Gln Val Leu Ile Tyr Arg Met Ser Asn Leu Ala Ser Gly Val Pro
         50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                 85                  90                  95

Leu Glu Tyr Pro Phe Thr Phe Gly Ser Gly Thr Lys Leu Glu Ile Lys
                100                 105                 110

Arg

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Tyr Tyr Met Tyr
 1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ile Asn Pro Ser Asn Gly Gly Thr Asn Phe Asn Glu Lys Phe Lys
 1               5                  10                  15

Ser

<210> SEQ ID NO 5
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 5

Gly Tyr Asp Arg Glu Trp Phe Ala Tyr
1               5

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Ser Lys Ser Leu Leu His Ser Asn Gly Asn Thr Tyr Leu Tyr
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Met Ser Asn Leu Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Gln His Leu Glu Tyr Pro Phe Thr
1               5

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
                20                  25                  30

Tyr Met Tyr Trp Val Lys Gln Ala Pro Gly Gln Gly Leu Glu Trp Ile
            35                  40                  45

Gly Gly Ile Asn Pro Ser Asn Gly Gly Thr Asn Phe Asn Glu Lys Phe
        50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
```

```
                85                  90                  95
Thr Arg Trp Gly Tyr Asp Arg Glu Trp Phe Ala Tyr Trp Gly Gln Gly
            100                 105                 110

Thr Leu Val Thr Val Ser Ser
            115

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Ser Lys Ala Thr Met Thr Val Asp Lys Ser Thr Ser Thr Ala Tyr
65                  70                  75                  80

Met Glu Leu Arg Ser Leu Arg Ser Asp Asp Ser Ala Val Tyr Tyr Cys
                85                  90                  95

Thr Arg Trp Gly Tyr Asp Arg Glu Trp Phe Ala Tyr Trp Gly Gln Gly
            100                 105                 110

Thr Leu Val Thr Val Ser Ser
            115

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Ser Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Gly Tyr Asp Arg Glu Trp Phe Ala Tyr Trp Gly Gln Gly
            100                 105                 110

Thr Leu Val Thr Val Ser Ser
            115
```

```
<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12
```

Asp Ile Val Met Thr Gln Ser Pro Ala Thr Leu Ser Val Ser Pro Gly
1               5                   10                  15

Glu Arg Ala Thr Ile Ser Cys Arg Ser Ser Lys Ser Leu Leu His Ser
            20                  25                  30

Asn Gly Asn Thr Tyr Leu Tyr Trp Phe Gln Gln Lys Pro Gly Gln Pro
        35                  40                  45

Pro Lys Val Leu Ile Tyr Arg Met Ser Asn Leu Ala Ser Gly Val Pro
    50                  55                  60

Ala Arg Phe Ser Gly Ser Gly Ser Gly Thr Asp Phe Thr Leu Thr Ile
65                  70                  75                  80

Ser Ser Val Glu Pro Glu Asp Phe Ala Thr Tyr Tyr Cys Met Gln His
                85                  90                  95

Leu Glu Tyr Pro Phe Thr Phe Gly Gly Gly Thr Lys Leu Glu Ile Lys
            100                 105                 110

Arg

```
<210> SEQ ID NO 13
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13
```

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110

Arg

```
<210> SEQ ID NO 14
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

Asp Ile Val Met Thr Gln Thr Pro Leu Ser Leu Ser Tyr Thr Pro Gly

```
                1               5                  10                  15
Gln Pro Ala Ser Ile Ser Cys Arg Ser Ser Lys Ser Leu Leu His Ser
                20                  25                  30

Asn Gly Asn Thr Tyr Leu Tyr Trp Phe Leu Gln Lys Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
                100                 105                 110

Arg

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr
            20                  25                  30

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Val Lys Gln Ala Pro Gly Gln Gly Leu Glu Trp Ile Gly
1               5                   10

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Lys Ala Thr Leu Thr Val Asp Lys Ser Ala Ser Thr Ala Tyr Met Glu
1               5                   10                  15

Leu Ser Ser Leu Arg Ser Glu Asp Thr Ala Val Tyr Tyr Cys Thr Arg
            20                  25                  30

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 18

Trp Gly Gln Gly Thr Leu Val Thr Val Ser Ser
1               5                   10

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Val Arg Gln Ala Pro Gly Gln Gly Leu Glu Trp Ile Gly
1               5                   10

<210> SEQ ID NO 21
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Lys Ala Thr Met Thr Val Asp Lys Ser Thr Ser Thr Ala Tyr Met Glu
1               5                   10                  15

Leu Arg Ser Leu Arg Ser Asp Asp Ser Ala Val Tyr Tyr Cys Thr Arg
            20                  25                  30

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Gly Gln Gly Thr Leu Val Thr Val Ser Ser
1               5                   10

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ala Glu Val Lys Lys Pro Gly Ser
```

```
1               5                   10                  15
Ser Val Lys Val Ser Cys Lys Ala Ser Gly Tyr Thr Phe Thr
                20                  25                  30

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Val Arg Gln Ala Pro Gly Gln Gly Leu Glu Trp Ile Gly
1               5                   10

<210> SEQ ID NO 25
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Lys Ala Thr Ile Thr Val Asp Lys Ser Thr Ser Thr Ala Tyr Met Glu
1               5                   10                  15
Leu Ser Ser Leu Arg Ser Glu Asp Thr Ala Val Tyr Tyr Cys Thr Arg
                20                  25                  30

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Gly Gln Gly Thr Leu Val Thr Val Ser Ser
1               5                   10

<210> SEQ ID NO 27
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Ile Val Met Thr Gln Ser Pro Ala Thr Leu Ser Val Ser Pro Gly
1               5                   10                  15
Glu Arg Ala Thr Ile Ser Cys
                20

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Phe Gln Gln Lys Pro Gly Gln Pro Pro Lys Val Leu Ile Tyr
```

```
<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Val Pro Ala Arg Phe Ser Gly Ser Gly Ser Gly Thr Asp Phe Thr
1               5                   10                  15

Leu Thr Ile Ser Ser Val Glu Pro Glu Asp Phe Ala Thr Tyr Tyr Cys
            20                  25                  30

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Gly Gly Gly Thr Lys Leu Glu Ile Lys Arg
1               5                   10

<210> SEQ ID NO 31
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Phe Leu Gln Lys Pro Gly Gln Ser Pro Gln Leu Leu Ile Tyr
1               5                   10                  15

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
```

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Phe Gly Gln Gly Thr Lys Leu Glu Ile Lys Arg
1               5                   10

<210> SEQ ID NO 35
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Asp Ile Val Met Thr Gln Thr Pro Leu Ser Leu Ser Tyr Thr Pro Gly
1               5                   10                  15

Gln Pro Ala Ser Ile Ser Cys
            20

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Trp Phe Leu Gln Lys Pro Gly Gln Ser Pro Gln Leu Leu Ile Tyr
1               5                   10                  15

<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Phe Gly Gln Gly Thr Lys Leu Glu Ile Lys Arg
1               5                   10

```
<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Lys Ala Thr Leu Thr Val Asp Lys Ser Ala Ser Thr Ala Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Lys Ala Thr Met Thr Val Asp Lys Ser Thr Ser Thr Ala Tyr Met Glu
1               5                   10                  15

Leu Arg Ser Leu Arg Ser Asp Asp Ser Ala Val Tyr Tyr Cys Ala Arg
                20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Lys Ala Thr Ile Thr Val Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 42
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Val Gln Ser Gly Ala Glu Val Lys Lys Pro Gly Ala
1               5                   10                  15

Ser Leu Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Ile
            35                  40                  45

Gly Gly Ile Asn Pro Ser Asn Gly Gly Thr Asn Phe Asn Glu Lys Phe
        50                  55                  60

Lys Gly Arg Val Thr Ile Thr Arg Asp Lys Ser Thr Ser Thr Ala Tyr
65                  70                  75                  80

Met Glu Leu Arg Ser Leu Arg Ser Glu Asp Ser Ala Val Tyr Tyr Cys
                85                  90                  95
```

```
Ala Arg Trp Gly Tyr Asp Arg Glu Trp Phe Ala Tyr Trp Gly Gln Gly
            100                 105                 110

Thr Leu Val Thr Val Ser Ser
        115

<210> SEQ ID NO 43
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Tyr Met Tyr Trp Val Lys Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Tyr Asp Arg Glu Trp Phe Ala Tyr Trp Gly Gln Gly
            100                 105                 110

Thr Leu Val Thr Val Ser Ser
        115

<210> SEQ ID NO 44
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Ser Lys Ala Thr Met Thr Val Asp Lys Ser Thr Ser Thr Ala Tyr
65                  70                  75                  80

Met Glu Leu Arg Ser Leu Arg Ser Asp Asp Ser Ala Val Tyr Tyr Cys
                85                  90                  95

Ala Arg Trp Gly Tyr Asp Arg Glu Trp Phe Ala Tyr Trp Gly Gln Gly
            100                 105                 110

Thr Leu Val Thr Val Ser Ser
        115

<210> SEQ ID NO 45
<211> LENGTH: 119
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Ile
            35                  40                  45

Gly Gly Ile Asn Pro Ser Asn Gly Gly Thr Asn Phe Asn Glu Lys Phe
        50                  55                  60

Lys Ser Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Tyr Asp Arg Glu Trp Phe Ala Tyr Trp Gly Gln Gly
            100                 105                 110

Thr Leu Val Thr Val Ser Ser
        115

<210> SEQ ID NO 46
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Lys Ser Leu Leu His Ser
                20                  25                  30

Asn Gly Asn Thr Tyr Leu Tyr Trp Tyr Gln Gln Lys Pro Gly Gln Ala
            35                  40                  45

Pro Arg Leu Leu Ile Tyr Arg Met Ser Asn Arg Ala Thr Gly Ile Pro
        50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Gln Gly Thr Lys Leu Glu Ile Lys
            100                 105                 110

Arg

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Met Lys Asn Met Asp Pro Leu Asn Asp Asn Val
1               5                   10
```

```
<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Met Lys Asn Met Asp Pro Leu Asn Asp Asn Ile
1               5                   10

<210> SEQ ID NO 49
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Arg Trp Gly Tyr Asp Arg Glu Trp Phe Ala Tyr Trp Gly Gln Gly
            100                 105                 110

Thr Leu Val Thr Val Ser Ser
        115

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Val Arg Gln Ala Pro Gly Gln Gly Leu Glu Trp Met Gly
1               5                   10

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Thr Arg
```

<210> SEQ ID NO 52
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 53
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Gly Tyr Asp Arg Glu Trp Phe Ala Tyr Trp Gly Gln Gly
            100                 105                 110

Thr Leu Val Thr Val Ser Ser
        115

<210> SEQ ID NO 54
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Tyr Met Tyr Trp Val Arg Gln Ala Pro Gly Gln Gly Leu
    50                  55                  60

Glu Trp Met Gly Gly Ile Asn Pro Ser Asn Gly Gly Thr Asn Phe Asn
65                  70                  75                  80

Glu Lys Phe Lys Ser Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Thr Arg Trp Gly Tyr Asp Arg Glu Trp Phe Ala Tyr Trp
        115                 120                 125

Gly Gln Gly Thr Leu Val Thr Val Ser Ser Ala Ser Thr Lys Gly Pro
130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Gln Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
450                 455                 460

Ser Pro Gly Lys
465

<210> SEQ ID NO 55
<211> LENGTH: 238

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Gly Trp Ser Cys Ile Ile Leu Phe Leu Val Ala Thr Ala Thr Gly
1               5                   10                  15
Val His Gly Asp Ile Val Met Thr Gln Ser Pro Leu Ser Leu Pro Val
            20                  25                  30
Thr Pro Gly Glu Pro Ala Ser Ile Ser Cys Arg Ser Ser Lys Ser Leu
        35                  40                  45
Leu His Ser Asn Gly Asn Thr Tyr Leu Tyr Trp Phe Leu Gln Lys Pro
    50                  55                  60
Gly Gln Ser Pro Gln Leu Leu Ile Tyr Arg Met Ser Asn Leu Ala Ser
65                  70                  75                  80
Gly Val Pro Asp Arg Phe Ser Gly Ser Gly Ser Gly Thr Ala Phe Thr
                85                  90                  95
Leu Lys Ile Ser Arg Val Glu Ala Glu Asp Val Gly Val Tyr Tyr Cys
            100                 105                 110
Met Gln His Leu Glu Tyr Pro Phe Thr Phe Gly Gln Gly Thr Lys Leu
        115                 120                 125
Glu Ile Lys Arg Thr Val Ala Ala Pro Ser Val Phe Ile Phe Pro Pro
    130                 135                 140
Ser Asp Glu Gln Leu Lys Ser Gly Thr Ala Ser Val Val Cys Leu Leu
145                 150                 155                 160
Asn Asn Phe Tyr Pro Arg Glu Ala Lys Val Gln Trp Lys Val Asp Asn
                165                 170                 175
Ala Leu Gln Ser Gly Asn Ser Gln Glu Ser Val Thr Glu Gln Asp Ser
            180                 185                 190
Lys Asp Ser Thr Tyr Ser Leu Ser Ser Thr Leu Thr Leu Ser Lys Ala
        195                 200                 205
Asp Tyr Glu Lys His Lys Val Tyr Ala Cys Glu Val Thr His Gln Gly
    210                 215                 220
Leu Ser Ser Pro Val Thr Lys Ser Phe Asn Arg Gly Glu Cys
225                 230                 235

<210> SEQ ID NO 56
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
caggtccaac tggtgcagtc tggggctgaa gtggtgaagc ctggggcttc agtgaagttg      60
tcctgcaagg cttctggcta caccttcacc agctactata tgtactgggt gaagcaggcg     120
cctggacaag ccttgagtg gattgggggg attaatccta gcaatggtgg tactaacttc     180
aatgagaagt tcaagagcaa ggccacactg actgtagaca atccgccag cacagcctac     240
atggaactca gcagcctgag atctgaggac actgcggtct attactgtac aagatgggggt     300
tacgacaggg agtggtttgc ttactggggc caagggactc tggtcactgt ctcttca        357

<210> SEQ ID NO 57
<211> LENGTH: 357
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
caggtccaac tggtgcagtc tggggctgaa gtgaagaagc ctggggcttc agtgaaggtg     60
tcctgcaagg cttctggcta caccttcacc agctactata tgtactgggt gaggcaggcg    120
cctggacaag gccttgagtg gattggggggg attaatccta gcaatggtgg tactaacttc   180
aatgagaagt tcaagagcaa ggccacaatg actgtagaca atccaccag cacagcctac     240 atggaactcc gcagcctgag atctgacgac actgcggtct attactgtac aagatggggt    300
tacgacaggg agtggtttgc ttactggggc caagggactc tggtcactgt ctcttca       357

<210> SEQ ID NO 58
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
caggtccaac tggtgcagtc tggggctgaa gtgaagaagc ctgggtcttc agtgaaggtg     60
tcctgcaagg cttctggcta caccttcacc agctactata tgtactgggt gaggcaggcg    120
cctggacaag gccttgagtg gattggggggg attaatccta gcaatggtgg tactaacttc   180
aatgagaagt tcaagagcaa ggccacaatc actgtagaca atccaccag cacagcctac     240 atggaactca gcagcctgag atctgaggac actgcggtct attactgtac aagatggggt    300
tacgacaggg agtggtttgc ttactggggc caagggactc tggtcactgt ctcttca       357

<210> SEQ ID NO 59
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
caggtccaac tggtgcagtc tggggctgaa gtgaagaagc ctggggcttc agtgaaggtg     60
tcctgcaagg cttctggcta caccttcacc agctactata tgtactgggt gaggcaggcg    120
cctggacaag gccttgagtg gatggggggg attaatccta gcaatggtgg tactaacttc    180
aatgagaagt tcaagagcag ggtcacaatg actacagaca catccaccag cacagcctac    240
atggaactcc gcagcctgag atctgacgac actgcggtct attactgtac aagatggggt    300
tacgacaggg agtggtttgc ttactggggc caagggactc tggtcactgt ctcttca       357

<210> SEQ ID NO 60
<211> LENGTH: 1508
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (53)..(1456)

<400> SEQUENCE: 60

-continued

```
cactataggg cgaattgaag gaaggccgtc aaggccgcat cctagggcca cc atg ggc          58
                                                        Met Gly
                                                          1 tgg tcc tgc atc atc ctg ttt ctg gtc gcc acc gcc acc ggc gtg cac           106
Trp Ser Cys Ile Ile Leu Phe Leu Val Ala Thr Ala Thr Gly Val His
          5                  10                  15 tcc cag gtc cag ctg gtc cag tct ggc gcc gaa gtg aag aaa cct ggc           154
Ser Gln Val Gln Leu Val Gln Ser Gly Ala Glu Val Lys Lys Pro Gly
         20                  25                  30 gcc tcc gtg aag gtg tcc tgc aag gcc tcc ggc tac acc ttc acc agc           202
Ala Ser Val Lys Val Ser Cys Lys Ala Ser Gly Tyr Thr Phe Thr Ser
 35                  40                  45                  50 tac tac atg tac tgg gtc cga cag gcc cca ggc cag gga ctg gaa tgg           250
Tyr Tyr Met Tyr Trp Val Arg Gln Ala Pro Gly Gln Gly Leu Glu Trp
                 55                  60                  65 atg ggc ggc atc aac ccc tcc aac ggc ggc acc aac ttc aac gag aag           298
Met Gly Gly Ile Asn Pro Ser Asn Gly Gly Thr Asn Phe Asn Glu Lys
             70                  75                  80 ttc aag tcc aga gtg acc atg acc acc gac acc tcc acc tcc acc gcc           346
Phe Lys Ser Arg Val Thr Met Thr Thr Asp Thr Ser Thr Ser Thr Ala
         85                  90                  95 tac atg gaa ctg cgg tcc ctg cgg agc gac gac acc gcc gtg tac tac           394
Tyr Met Glu Leu Arg Ser Leu Arg Ser Asp Asp Thr Ala Val Tyr Tyr
        100                 105                 110 tgc acc aga tgg ggc tac gac aga gag tgg ttc gcc tac tgg ggc cag           442
Cys Thr Arg Trp Gly Tyr Asp Arg Glu Trp Phe Ala Tyr Trp Gly Gln
115                 120                 125                 130 ggc acc ctg gtc aca gtg tcc tcc gct tcc acc aag ggc ccc tcc gtg           490
Gly Thr Leu Val Thr Val Ser Ser Ala Ser Thr Lys Gly Pro Ser Val
                135                 140                 145 ttc cct ctg gcc ccc tcc agc aag tcc acc tct ggc ggc acc gct gcc           538
Phe Pro Leu Ala Pro Ser Ser Lys Ser Thr Ser Gly Gly Thr Ala Ala
            150                 155                 160 ctg ggc tgc ctg gtc aaa gac tac ttc ccc gag ccc gtg acc gtg tcc           586
Leu Gly Cys Leu Val Lys Asp Tyr Phe Pro Glu Pro Val Thr Val Ser
        165                 170                 175 tgg aac tct ggc gcc ctg acc agc ggc gtg cac acc ttc cct gcc gtg           634
Trp Asn Ser Gly Ala Leu Thr Ser Gly Val His Thr Phe Pro Ala Val
    180                 185                 190 ctg cag tct tcc ggc ctg tac tcc ctg tcc tcc gtg gtc acc gtg ccc           682
Leu Gln Ser Ser Gly Leu Tyr Ser Leu Ser Ser Val Val Thr Val Pro
195                 200                 205                 210 tcc agc tct ctg ggc acc cag acc tac atc tgc aac gtg aac cac aag           730
Ser Ser Ser Leu Gly Thr Gln Thr Tyr Ile Cys Asn Val Asn His Lys
                215                 220                 225 ccc tcc aac acc aag gtg gac aag cgg gtg gaa ccc aag tcc tgc gac           778
Pro Ser Asn Thr Lys Val Asp Lys Arg Val Glu Pro Lys Ser Cys Asp
            230                 235                 240 aag acc cac acc tgt ccc ccc tgc cct gcc cct gaa ctg ctg ggc gga           826
Lys Thr His Thr Cys Pro Pro Cys Pro Ala Pro Glu Leu Leu Gly Gly
        245                 250                 255 cct tcc gtg ttc ctg ttc ccc cca aag ccc aag gac acc ctg atg atc           874
Pro Ser Val Phe Leu Phe Pro Pro Lys Pro Lys Asp Thr Leu Met Ile
    260                 265                 270 tcc cgg acc ccc gaa gtg acc tgc gtg gtg gtg gac gtg tcc cac gag           922
Ser Arg Thr Pro Glu Val Thr Cys Val Val Val Asp Val Ser His Glu
275                 280                 285                 290 gac cct gaa gtg aag ttc aat tgg tac gtg gac ggc gtg gaa gtg cac           970
Asp Pro Glu Val Lys Phe Asn Trp Tyr Val Asp Gly Val Glu Val His
```

|  |  |  |  |  |  |  |  |  |  |  |  |  |  |  |  |  |
|---|---|---|---|---|---|---|---|---|---|---|---|---|---|---|---|---|
|  |  |  |  | 295 |  |  |  |  | 300 |  |  |  |  | 305 |  |  |
| aac | gcc | aag | acc | aag | ccc | aga | gag | gaa | cag | tac | cag | tcc | acc | tac | cgg | 1018 |
| Asn | Ala | Lys | Thr | Lys | Pro | Arg | Glu | Glu | Gln | Tyr | Gln | Ser | Thr | Tyr | Arg |  |
|  |  |  |  | 310 |  |  |  |  | 315 |  |  |  |  | 320 |  |  |
| gtg | gtg | tct | gtg | ctg | acc | gtg | ctg | cac | cag | gac | tgg | ctg | aac | ggc | aaa | 1066 |
| Val | Val | Ser | Val | Leu | Thr | Val | Leu | His | Gln | Asp | Trp | Leu | Asn | Gly | Lys |  |
|  |  |  |  | 325 |  |  |  |  | 330 |  |  |  |  | 335 |  |  |
| gag | tac | aag | tgc | aag | gtc | tcc | aac | aag | gcc | ctg | cct | gcc | ccc | atc | gaa | 1114 |
| Glu | Tyr | Lys | Cys | Lys | Val | Ser | Asn | Lys | Ala | Leu | Pro | Ala | Pro | Ile | Glu |  |
|  |  |  | 340 |  |  |  |  | 345 |  |  |  |  | 350 |  |  |  |
| aag | acc | atc | tcc | aag | gcc | aag | ggc | cag | ccc | cgc | gag | ccc | cag | gtg | tac | 1162 |
| Lys | Thr | Ile | Ser | Lys | Ala | Lys | Gly | Gln | Pro | Arg | Glu | Pro | Gln | Val | Tyr |  |
| 355 |  |  |  |  | 360 |  |  |  |  | 365 |  |  |  |  | 370 |  |
| aca | ctg | ccc | cct | agc | cgg | gaa | gag | atg | acc | aag | aac | cag | gtg | tcc | ctg | 1210 |
| Thr | Leu | Pro | Pro | Ser | Arg | Glu | Glu | Met | Thr | Lys | Asn | Gln | Val | Ser | Leu |  |
|  |  |  |  | 375 |  |  |  |  | 380 |  |  |  |  | 385 |  |  |
| acc | tgt | ctg | gtc | aaa | ggc | ttc | tac | ccc | tcc | gac | att | gcc | gtg | gaa | tgg | 1258 |
| Thr | Cys | Leu | Val | Lys | Gly | Phe | Tyr | Pro | Ser | Asp | Ile | Ala | Val | Glu | Trp |  |
|  |  |  | 390 |  |  |  |  | 395 |  |  |  |  | 400 |  |  |  |
| gag | tcc | aac | ggc | cag | ccc | gag | aac | aac | tac | aag | acc | acc | ccc | cct | gtg | 1306 |
| Glu | Ser | Asn | Gly | Gln | Pro | Glu | Asn | Asn | Tyr | Lys | Thr | Thr | Pro | Pro | Val |  |
|  |  | 405 |  |  |  |  | 410 |  |  |  |  | 415 |  |  |  |  |
| ctg | gac | tcc | gac | ggc | tca | ttc | ttc | ctg | tac | tcc | aag | ctg | acc | gtg | gac | 1354 |
| Leu | Asp | Ser | Asp | Gly | Ser | Phe | Phe | Leu | Tyr | Ser | Lys | Leu | Thr | Val | Asp |  |
| 420 |  |  |  |  | 425 |  |  |  |  | 430 |  |  |  |  |  |  |
| aag | tcc | cgg | tgg | cag | cag | ggc | aac | gtg | ttc | tcc | tgc | tcc | gtg | atg | cac | 1402 |
| Lys | Ser | Arg | Trp | Gln | Gln | Gly | Asn | Val | Phe | Ser | Cys | Ser | Val | Met | His |  |
| 435 |  |  |  |  | 440 |  |  |  |  | 445 |  |  |  |  | 450 |  |
| gag | gcc | ctg | cac | aac | cac | tac | acc | cag | aag | tcc | ctg | tcc | ctg | agc | ccc | 1450 |
| Glu | Ala | Leu | His | Asn | His | Tyr | Thr | Gln | Lys | Ser | Leu | Ser | Leu | Ser | Pro |  |
|  |  |  |  | 455 |  |  |  |  | 460 |  |  |  |  | 465 |  |  |
| ggc | aag | tgatgagtat | acctgggcct | catgggcctt | cctttcactg | cccgctttcc | ag |  |  |  |  |  |  |  |  | 1508 |
| Gly | Lys |  |  |  |  |  |  |  |  |  |  |  |  |  |  |  |

<210> SEQ ID NO 61
<211> LENGTH: 338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gatattgtga tgactcagtc tccagccact ctatctgtct ctcctggaga gcgagcaacc    60
atctcctgca gggctagtaa gagtctcctg catagtaatg caacacttta cttgtattgg   120
ttccagcaga agccaggcca gcctcctaag gtcctgatat atcggatgtc aaccttgcc    180 tcaggagtcc cagccaggtt cagtggcagt gggtcaggaa ctgatttcac actgacaatc   240
agttcggtgg agcctgagga ttttgctact tattactgta tgcaacatct agaatatcca   300
ttcacgttcg gcgggggac aaagttggaa ataaaacg                            338

<210> SEQ ID NO 62
<211> LENGTH: 338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
gatattgtga tgactcagtc tccactctct ctacctgtca ctcctggaga gccagcatcc    60
atctcctgca ggtctagtaa gagtctcctg catagtaatg caacactta cttgtattgg   120 ttcctgcaga agccaggcca gtctcctcag ctcctgatat atcggatgtc caaccttgcc   180
tcaggagtcc cagacaggtt cagtggcagt gggtcaggaa ctgctttcac actgaaaatc   240
agtagagtgg aggctgagga tgtgggtgtt tattactgta tgcaacatct agaatatcca   300
ttcacgttcg gccaggggac aaagctggaa ataaaacg                           338
```

```
<210> SEQ ID NO 63
<211> LENGTH: 338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gatattgtga tgactcagac tccactctct ctatctgtca ctcctggaca gccagcatcc    60
atctcctgca ggtctagtaa gagtctcctg catagtaatg caacactta cttgtattgg   120 ttcctgcaga agccaggcca gtctcctcag ctcctgatat atcggatgtc caaccttgcc   180
tcaggagtcc cagacaggtt cagtggcagt gggtcaggaa ctgatttcac actgaaaatc   240
agtagagtgg aggctgagga tgtgggtgtt tattactgta tgcaacatct agaatatcca   300
ttcacgttcg gccaggggac aaagctggaa ataaaacg                           338
```

```
<210> SEQ ID NO 64
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
caggtccagc tggtccagtc tggcgccgaa gtgaagaaac ctggcgcctc cgtgaaggtg    60
tcctgcaagg cctccggcta caccttcacc agctactaca tgtactgggt ccgacaggcc   120
ccaggccagg gactggaatg gatgggcggc atcaaccct ccaacggcgg caccaacttc   180
aacgagaagt tcaagtccag agtgaccatg accaccgaca cctccacctc caccgcctac   240
atggaactgc ggtccctgcg gagcgacgac accgccgtgt actactgcac cagatggggc   300
tacgacagag agtggttcgc ctactggggc cagggcaccc tggtcacagt gtcctcc      357
```

```
<210> SEQ ID NO 65
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gacatcgtga tgacccagtc ccccctgtcc ctgcccgtga cacctggcga gcctgcctcc    60
atctcctgcc ggtcctccaa gtccctgctg cactccaacg gcaataccta cctgtactgg   120
ttcctgcaga agcccggcca gtcccctcag ctgctgatct accggatgtc caacctggcc   180
tccggcgtgc ccgacagatt ctccggctct ggctctggca gccttcac cctgaagatc   240 tcccgggtgg aagccgagga cgtgggcgtg tactactgca tgcagcacct ggaataccc   300
```

```
ttcaccttcg gccagggcac caagctggaa atcaagcgg                          339
```

<210> SEQ ID NO 66
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
atgggatggt catgtatcat ccttttctta gtagcaactg caaccggtgt ccactcccag    60
gtccaactgg tgcagtctgg ggctgaagtg aagaagcctg ggcttcagt gaaggtgtcc    120
tgcaaggctt ctggctacac cttcaccagc tactatatgt actgggtgag gcaggcgcct   180
ggacaaggcc ttgagtggat ggggggggatt aatcctagca atggtggtac taacttcaat   240
gagaagttca gagcagggt cacaatgact acagacacat ccaccagcac agcctacatg    300
gaactccgca gcctgagatc tgacgacact gcggtctatt actgtacaag atggggttac    360
gacagggagt ggtttgctta ctggggccaa gggactctgg tcactgtctc ttcagcgtcg   420
accaagggcc catcggtctt ccccctggca ccctcctcca agagcacctc tgggggcaca    480
gcggccctgg gctgcctggt caaggactac ttccccgaac ctgtgacggt ctcgtggaac    540
tcaggcgccc tgaccagcgg cgtgcacacc ttcccggctg tcctacagtc ctcaggactc    600
tactccctca gcagcgtggt gaccgtgccc tccagcagct gggcaccca gacctacatc    660
tgcaacgtga atcacaagcc cagcaacacc aaggtggaca gagagttga gcccaaatct    720
tgtgacaaaa ctcacacatg cccaccgtgc ccagcacctg aactcctggg gggaccgtca    780
gtcttcctct ccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca aagccgcggg aggagcagta ccagagcacg    960
taccgtgtgg tcagcgtcct caccgtcctg caccaggact ggctgaatgg caaggagtac   1020
aagtgcaagg tctccaacaa agccctccca gcccccatcg agaaaaccat ctccaaagcc   1080
aaagggcagc cccgagaacc acaggtgtac accctgcccc catcccggga ggagatgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
tccgacggct ccttcttcct ctatagcaag ctcaccgtgg acaagagcag gtggcagcag   1320
gggaacgtct tctcatgctc cgtgatgcat gaggctctgc acaaccacta cacgcagaag   1380
agcctctccc tgtccccggg taaatga                                       1407
```

<210> SEQ ID NO 67
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
atgggatggt catgtatcat ccttttctta gtagcaactg caaccggtgt acatggggat    60
attgtgatga ctcagtctcc actctctcta cctgtcactc ctggagagcc agcatccatc   120
tcctgcaggt ctagtaagag tctcctgcat agtaatggca acacttactt gtattggttc    180
ctgcagaagc caggccagtc tcctcagctc ctgatatatc ggatgtccaa ccttgcctca    240
```

```
ggagtcccag acaggttcag tggcagtggg tcaggaactg ctttcacact gaaaatcagt    300
agagtggagg ctgaggatgt gggtgtttat tactgtatgc aacatctaga atatccattc    360
acgttcggcc aggggacaaa gctggaaata aaacgtacgg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctacgc ctgcgaagtc     660 acccatcagg gcctgagctc gcccgtcaca aagagcttca caggggaga gtgttag       717
```

<210> SEQ ID NO 68
<211> LENGTH: 1456
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 68

```
atgggctggt cctgcatcat cctgtttctg gtcgccaccg ccaccggcgt gcactcccag     60
gtccagctgg tccagtctgg cgccgaagtg aagaaacctg gcgcctccgt gaaggtgtcc    120
tgcaaggcct ccggctacac cttcaccagc tactacatgt actgggtccg acaggcccca    180
ggccagggac tggaatggat gggcggcatc aacccctcca cggcggcac caacttcaac    240 gagaagttca gtccagagt gaccatgacc accgacacct ccacctccac cgcctacatg    300
gaactgcggt ccctgcggag cgacgacacc gccgtgtact actgcaccag atggggctac    360
gacagagagt ggttcgccta ctggggccag ggcaccctgg tcacagtgtc ctccgcttcc    420
accaagggcc cctccgtgtt ccctctggcc ccctccagca gtccacctc tggcggcacc    480 gctgccctgg gctgcctggt caaagactac ttccccgagc ccgtgaccgt gtcctggaac    540
tctggcgccc tgaccagcgg cgtgcacacc ttcctgccg tgctgcagtc ttccggcctg    600
tactccctgt cctccgtggt caccgtgccc tccagctctc tgggcaccca gacctacatc    660
tgcaacgtga accacaagcc ctccaacacc aaggtggaca agcgggtgga acccaagtcc    720
tgcgacaaga cccacacctg tcccccctgc cctgcccctg aactgctggg cggaccttcc    780
gtgttcctgt tccccccaaa gcccaaggac accctgatga tctcccggac ccccgaagtg    840
acctgcgtgt ggtggacgt gtcccacgag gaccctgaag tgaagttcaa ttggtacgtg    900
gacggcgtgg aagtgcacaa cgccaagacc aagcccagag aggaacagta ccagtccacc    960
taccgggtgg tgtctgtgct gaccgtgctg caccaggact ggctgaacgg caaagagtac   1020
aagtgcaagg tctccaacaa ggccctgcct gcccccatcg aaaagaccat ctccaaggcc   1080
aagggccagc ccgcgagcc ccaggtgtac acactgcccc ctagccggga agagatgacc    1140
aagaaccagg tgtccctgac ctgtctggtc aaaggcttct acccctccga cattgccgtg   1200
gaatgggagt ccaacggcca gcccgagaac aactacaaga ccacccccc tgtgctggac   1260 tccgacggct cattcttcct gtactccaag ctgaccgtgg acaagtcccg gtggcagcag   1320
ggcaacgtgt tctcctgctc cgtgatgcac gaggccctgc acaaccacta cacccagaag   1380
tccctgtccc tgagccccgg caagtgatga gtatacctgg gcctcatggg ccttcctttc   1440
actgcccgct ttccag                                                    1456
```

<210> SEQ ID NO 69
<211> LENGTH: 832
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (59)..(772)

<400> SEQUENCE: 69

```
cgaattggcg gaaggccgtc aaggccacgt gtcttgtcca gagctcgata tcgccacc            58 atg ggc tgg tcc tgc atc atc ctg ttt ctg gtc gcc acc gcc acc ggc          106
Met Gly Trp Ser Cys Ile Ile Leu Phe Leu Val Ala Thr Ala Thr Gly
 1               5                  10                  15 gtg cac ggc gac atc gtg atg acc cag tcc ccc ctg tcc ctg ccc gtg         154
Val His Gly Asp Ile Val Met Thr Gln Ser Pro Leu Ser Leu Pro Val
            20                  25                  30 aca cct ggc gag cct gcc tcc atc tcc tgc cgg tcc tcc aag tcc ctg         202
Thr Pro Gly Glu Pro Ala Ser Ile Ser Cys Arg Ser Ser Lys Ser Leu
        35                  40                  45 ctg cac tcc aac ggc aat acc tac ctg tac tgg ttc ctg cag aag ccc         250
Leu His Ser Asn Gly Asn Thr Tyr Leu Tyr Trp Phe Leu Gln Lys Pro
    50                  55                  60 ggc cag tcc cct cag ctg ctg atc tac cgg atg tcc aac ctg gcc tcc         298
Gly Gln Ser Pro Gln Leu Leu Ile Tyr Arg Met Ser Asn Leu Ala Ser
65                  70                  75                  80 ggc gtg ccc gac aga ttc tcc ggc tct ggc tct ggc aca gcc ttc acc         346
Gly Val Pro Asp Arg Phe Ser Gly Ser Gly Ser Gly Thr Ala Phe Thr
                85                  90                  95 ctg aag atc tcc cgg gtg gaa gcc gag gac gtg ggc gtg tac tac tgc         394
Leu Lys Ile Ser Arg Val Glu Ala Glu Asp Val Gly Val Tyr Tyr Cys
            100                 105                 110 atg cag cac ctg gaa tac ccc ttc acc ttc ggc cag ggc acc aag ctg         442
Met Gln His Leu Glu Tyr Pro Phe Thr Phe Gly Gln Gly Thr Lys Leu
        115                 120                 125 gaa atc aag cgg acc gtg gcc gct ccc tcc gtg ttc atc ttc cca ccc         490
Glu Ile Lys Arg Thr Val Ala Ala Pro Ser Val Phe Ile Phe Pro Pro
    130                 135                 140 tcc gac gag cag ctg aag tcc ggc acc gcc tcc gtc gtc tgc ctg ctg         538
Ser Asp Glu Gln Leu Lys Ser Gly Thr Ala Ser Val Val Cys Leu Leu
145                 150                 155                 160 aac aac ttc tac ccc cgc gag gcc aag gtg cag tgg aag gtg gac aac         586
Asn Asn Phe Tyr Pro Arg Glu Ala Lys Val Gln Trp Lys Val Asp Asn
                165                 170                 175 gcc ctg cag tcc ggc aac tcc cag gaa tcc gtc acc gag cag gac tcc         634
Ala Leu Gln Ser Gly Asn Ser Gln Glu Ser Val Thr Glu Gln Asp Ser
            180                 185                 190 aag gac agc acc tac tcc ctg tct tcc acc ctg acc ctg tcc aag gcc         682
Lys Asp Ser Thr Tyr Ser Leu Ser Ser Thr Leu Thr Leu Ser Lys Ala
        195                 200                 205 gac tac gag aag cac aag gtg tac gcc tgc gaa gtg acc cac cag ggc         730
Asp Tyr Glu Lys His Lys Val Tyr Ala Cys Glu Val Thr His Gln Gly
    210                 215                 220 ctg tcc agc ccc gtg acc aag tcc ttc aac cgg ggc gag tgc                 772
Leu Ser Ser Pro Val Thr Lys Ser Phe Asn Arg Gly Glu Cys
225                 230                 235 tgatgattaa ttaaggtacc tggagcacaa gactggcctc atgggccttc cgctcactgc       832
```